United States Patent
Kang et al.

(10) Patent No.: US 11,730,766 B2
(45) Date of Patent: Aug. 22, 2023

(54) COMPOSITION FOR PREVENTING OR TREATING INFLAMMATORY DISEASES, CONTAINING, AS ACTIVE INGREDIENT, STEM CELLS OVEREXPRESSING SOD3

(71) Applicant: KANGSTEM BIOTECH CO., LTD., Seoul (KR)

(72) Inventors: Kyung Sun Kang, Seoul (KR); Tae Yoon Kim, Seoul (KR)

(73) Assignee: KANGSTEM BIOTECH CO., LTD.

( * ) Notice: Subject to any disclaimer, the term of this patent is extended or adjusted under 35 U.S.C. 154(b) by 49 days.

(21) Appl. No.: 15/760,106

(22) PCT Filed: Sep. 19, 2016

(86) PCT No.: PCT/KR2016/010414
§ 371 (c)(1),
(2) Date: Jun. 15, 2018

(87) PCT Pub. No.: WO2017/048097
PCT Pub. Date: Mar. 23, 2017

(65) Prior Publication Data
US 2018/0344774 A1 Dec. 6, 2018

(30) Foreign Application Priority Data
Sep. 15, 2015 (KR) .................. 10-2015-0130377

(51) Int. Cl.
*A61K 35/28* (2015.01)
*C12N 15/85* (2006.01)
*A61K 35/50* (2015.01)
*A61K 35/51* (2015.01)
*A61P 17/00* (2006.01)
*A61K 38/44* (2006.01)

(52) U.S. Cl.
CPC .............. *A61K 35/28* (2013.01); *A61K 35/50* (2013.01); *A61K 35/51* (2013.01); *A61K 38/446* (2013.01); *A61P 17/00* (2018.01); *C12N 15/85* (2013.01); *C12Y 115/01001* (2013.01); *Y02A 50/30* (2018.01)

(58) Field of Classification Search
CPC ........ A61K 35/28; A61K 35/50; A61K 35/51; A61K 38/446; A61K 35/5104; C12N 15/85; A61P 17/00; C12Y 115/01001; Y02A 50/30
See application file for complete search history.

(56) References Cited

U.S. PATENT DOCUMENTS

| | | | | |
|---|---|---|---|---|
| 5,994,339 A * | 11/1999 | Crapo | .................. | A01K 67/0278 514/185 |
| 6,127,356 A * | 10/2000 | Crapo | ..................... | A61K 31/00 252/399 |
| 2011/0225661 A1 * | 9/2011 | Deng | .................. | A01K 67/0275 800/9 |
| 2012/0093796 A1 * | 4/2012 | Shin | ...................... | A61K 38/446 424/94.4 |
| 2012/0201791 A1 | 8/2012 | June | | |
| 2012/0269774 A1 | 10/2012 | Ichim et al. | | |
| 2015/0038496 A1 * | 2/2015 | Amigorena | ............. | A61P 11/06 506/10 |

FOREIGN PATENT DOCUMENTS

| | | |
|---|---|---|
| CN | 101678074 A | 3/2010 |
| CN | 102660580 A | 9/2012 |
| EP | 2298861 A2 | 3/2011 |
| JP | 2001136985 A * | 5/2001 |
| JP | 2010522159 A | 7/2010 |
| KR | 100676502 B1 | 2/2007 |
| KR | 101019470 B1 | 3/2011 |
| KR | 170043793 A | 4/2017 |

OTHER PUBLICATIONS

Yu et al. "Over-expression of extracellular superoxide dismutase in mouse synovial tissue attenuates the inflammatory arthritis."Exp Mol Med. Sep. 30, 2012;44(9):529-35. (Year: 2012).*
Gan et al. "Hematopoietic recovery of acute radiation syndrome by human superoxide dismutase-expressing umbilical cord mesenchymal stromal cells."Cytotherapy. Apr. 2015;17(4):403-17. (Year: 2015).*
Kim et al. "Regulation of skin inflammation and angiogenesis by EC-SOD via HIF-1α and NF-κB pathways."Free Radic Biol Med. Dec. 1, 2011;51(11):1985-95 (Year: 2011).*
Tokura et al. "Psoriasis and other Th17-mediated skin diseases." J Uoeh. Dec. 1, 2010;32(4):317-28. (Year: 2010).*
Liang et al. "Human Umbilical Cord Mesenchymal Stem Cells Ameliorate Mice Trinitrobenzene Sulfonic Acid (TNBS)-Induced Colitis."Cell Transplant. 2011;20(9):1395-408. (Year: 2011).*
Noda et al. "The translational revolution and use of biologies in patients with inflammatory skin diseases."J Allergy Clin Immunol . Feb. 2015;135(2):324-36. (Year: 2015).*
Starace et al. "Erosive pustular dermatosis of the scalp: challenges and solutions." Clin Cosmet Investig Dermatol. Sep. 12, 2019;12:691-698. (Year: 2019).*

(Continued)

*Primary Examiner* — Titilayo Moloye
(74) *Attorney, Agent, or Firm* — Levenfeld Pearlstein, LLC

(57) ABSTRACT

The present invention provides a pharmaceutical composition for preventing or treating inflammatory diseases, containing, as an active ingredient, stem cells overexpressing SOD3. The present inventor has ascertained that mesenchymal stem cells (MSCs) overexpressing SOD3 have a stronger antioxidant activity and immune regulatory function than normal MSCs, and thus the MSCs overexpressing SOD3 can be an effective treatment agent for inflammatory diseases, autoimmune diseases, organ transplant rejection and the like.

6 Claims, 21 Drawing Sheets
Specification includes a Sequence Listing.

(56) References Cited

OTHER PUBLICATIONS

Wolina et al. "Anetoderma Schweninger-Buzzi: Two Case Reports." Open Access Maced J Med Sci. Sep. 30, 2019; 7(18): 3093-3095. (Year: 2019).*

Cook et al. "Anetoderma." Jan. 2, 2022. In: StatPearls [Internet], Treasure Island (FL): StatPearls Publishing; Jan. 2022—. PMID: 32809440. (Year: 2022).*

Setoguchi et al. "Ex vivo and in vivo gene transfer to the skin using replication-deficient recombinant adenovirus vectors." J Invest Dermatol. Apr. 1994;102(4):415-21. (Year: 1994).*

Na et al. "Bone marrow-derived clonal mesenchymal stem cells inhibit ovalbumin-induced atopic dermatitis."Cell Death Dis. Jul. 17, 2014;5(7):e1345. (Year: 2014).*

Kwon, Myung-Ja et al., Superoxide Dismutase 3 Controls Adaptive Immune Responses and Contributes to the Inhibition of Ovalbumin-Induced Allergic Airway Inflammation in Mice, Antioxidants & Redox Signaling, Sep. 11, 2012, pp. 1376-1392, vol. 17, No. 10, Mary Ann Liebert, Inc., New Rochelle, NY.

SOD3 superoxide dismutase 3 [*Homo sapiens* (human)], HUGO Gene Nomenclature Committee, Updated Apr. 16, 2018, NCBI, GenBank accession No. AAA66000.1.

Halleck, A., et al., *Homo sapiens* full open reading frame cDNA clone RZPDo834H0432D for gene SOD3, superoxide dismutase 3, extracellular; complete cds, incl. stopcodon, National Center for Biotechnology Information, Jun. 28, 2004, NCBI, GenBank accession No. CR541853.1.

Kemp, Kevin et al., Inflammatory Cytokine Induced Regulation of Superoxide Dismutase 3 Expression by Human Mesenchymal Stem Cells, Stem Cell Reviews and Reports, Dec. 2010, pp. 548-559, vol. 6, Issue 4, Humana Press Inc, New York City, NY.

Kishor, Sah Shyam et al., Effects of Human Mesenchymal Stem Cells Transduced with Superoxide Dismutase on Imiquimod-Induced Psoriasis-Like Skin Inflammation in Mice, Antioxidants & Redox Signaling, Feb. 3, 2016, pp. 233-248, vol. 24, No. 5, Mary Ann Liebert, Inc., New Rochelle, NY.

Kwon, Myung-Ja et al., Superoxide Dismutase 3 Controls Adaptive Immune Responses and Contributes to the Inhibition of Ovalbumin-Induced Allergic Airway Inflammation in Mice, Antioxidants & Redox Signaling, 2012, pp. 1376-1392, vol. 17, No. 10, Mary Ann Liebert, Inc., New Rochelle, NY.

Na, K et al., Bone Marrow-Derived Clonal Mesenchymal Stem Cells Inhibit Ovalbumin-Induced Atopic Dermatitis, Cell Dealth and Disease, 2014, pp. 1-11, vol. 5, Macmillan Publishers Limited, New York.

Superoxide dismutase [Humo sapiens], NCBI, GenBank: AAA62278. 1.

Lim, Ji-Young et al., The therapeutic efficacy of mesenchymal stromal cells on experimental colitis was improved by the IFN-y and poly(I:C) priming through promoting the expression of indoleamine 2,3-dioxygenase, Stem Cell Research & Therapy, 2021, pp. 1-13, vol. 12, No. 37. Republic of Korea.

Kim, Hyung-Sik et al., Human Umbilical Cord Blood Mesenchymal Stem Cells Reduce Colitis in Mice by Activating NOD2 Signaling to COX2, Gastroenterology, Dec. 2013, pp. 1392-1403.

Li, Dong et al., Overexpression of COX-2 but not indoleamine 2,3-dioxygenase-1 enhances the immunosuppressive ability of human umbilical cord-derived mesenchymal stem cells, International Journal of Molecular Medicine, 2015, pp. 1309-1316.

* cited by examiner

SEQUENCE LISTING

```
<160> NUMBER OF SEQ ID NOS: 32

<210> SEQ ID NO 1
<211> LENGTH: 240
<212> TYPE: PRT
<213> ORGANISM: Artificial Sequence
<220> FEATURE:
<223> OTHER INFORMATION: human SOD3 protein

<400> SEQUENCE: 1

Met Leu Ala Leu Leu Cys Ser Cys Leu Leu Leu Ala Ala Gly Ala Ser
1               5                   10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
        35                  40                  45

Val Met Gln Arg Arg Asp Asp Asp Gly Thr Leu His Ala Ala Cys Gln
    50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Ser Arg Ala
            100                 105                 110

Ile His Val His Gln Phe Gly Asp Leu Ser Gln Gly Cys Glu Ser Thr
        115                 120                 125

Gly Pro His Tyr Asn Pro Leu Ala Val Pro His Pro Gln His Pro Gly
    130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175

Ala Val Val Val His Ala Gly Glu Asp Asp Leu Gly Arg Gly Gly Asn
            180                 185                 190

Gln Ala Ser Val Glu Asn Gly Asn Ala Gly Arg Arg Leu Ala Cys Cys
        195                 200                 205

Val Val Gly Val Cys Gly Pro Gly Leu Trp Glu Arg Gln Ala Arg Glu
    210                 215                 220

His Ser Glu Arg Lys Lys Arg Arg Glu Ser Glu Cys Lys Ala Ala
225                 230                 235                 240

<210> SEQ ID NO 2
<211> LENGTH: 720
<212> TYPE: DNA
```

-continued

<213> ORGANISM: Artificial Sequence
<220> FEATURE:
<223> OTHER INFORMATION: human SOD3 DNA

<400> SEQUENCE: 2

```
atgctggcgc tactgtgttc ctgcctgctc ctggcagccg gtgcctcgga cgcctggacg     60
ggcgaggact cggcggagcc caactctgac tcggcggagt ggatccgaga catgtacgcc    120
aaggtcacgg agatctggca ggaggtcatg cagcggcggg acgacgacgg cacgctccac    180
gccgcctgcc aggtgcagcc gtcggccacg ctggacgccg cgcagccccg ggtgaccggc    240
gtcgtcctct tccggcagct tgcgccccgc gccaagctcg acgccttctt cgccctggag    300
ggcttcccga ccgagccgaa cagctccagc cgcgccatcc acgtgcacca gttcggggac    360
ctgagccagg gctgcgagtc caccgggccc cactacaacc cgctggccgt gccgcacccg    420
cagcacccgg gcgacttcgg caacttcgcg gtccgcgacg gcagcctctg gaggtaccgc    480
gccggcctgg ccgcctcgct cgcgggcccg cactccatcg tgggccgggc cgtggtcgtc    540
cacgctggcg aggacgacct gggccgcggc ggcaaccagg ccagcgtgga gaacgggaac    600
gcgggccggc ggctggcctg ctgcgtggtg ggcgtgtgcg ggcccgggct ctgggagcgc    660
caggcgcggg agcactcaga gcgcaagaag cggcggcgcg agagcgagtg caaggccgcc    720
```

<210> SEQ ID NO 3
<211> LENGTH: 209
<212> TYPE: PRT
<213> ORGANISM: Artificial Sequence
<220> FEATURE:
<223> OTHER INFORMATION: 209E-SOD3 protein

<400> SEQUENCE: 3

```
Trp Thr Gly Glu Asp Ser Ala Glu Pro Asn Ser Asp Ser Ala Glu Trp
1               5                   10                  15

Ile Arg Asp Met Tyr Ala Lys Val Thr Glu Ile Trp Gln Glu Val Met
            20                  25                  30

Gln Arg Arg Asp Asp Asp Gly Thr Leu His Ala Ala Cys Gln Val Gln
        35                  40                  45

Pro Ser Ala Thr Leu Asp Ala Ala Gln Pro Arg Val Thr Gly Val Val
    50                  55                  60

Leu Phe Arg Gln Leu Ala Pro Arg Ala Lys Leu Asp Ala Phe Phe Ala
65                  70                  75                  80

Leu Glu Gly Phe Pro Thr Glu Pro Asn Ser Ser Ser Arg Ala Ile His
                85                  90                  95

Val His Gln Phe Gly Asp Leu Ser Gln Gly Cys Glu Ser Thr Gly Pro
            100                 105                 110

His Tyr Asn Pro Leu Ala Val Pro His Pro Gln His Pro Gly Asp Phe
        115                 120                 125

Gly Asn Phe Ala Val Arg Asp Gly Ser Leu Trp Arg Tyr Arg Ala Gly
    130                 135                 140

Leu Ala Ala Ser Leu Ala Gly Pro His Ser Ile Val Gly Arg Ala Val
145                 150                 155                 160

Val Val His Ala Gly Glu Asp Asp Leu Gly Arg Gly Gly Asn Gln Ala
                165                 170                 175

Ser Val Glu Asn Gly Asn Ala Gly Arg Arg Leu Ala Cys Cys Val Val
            180                 185                 190

Gly Val Cys Gly Pro Gly Leu Trp Glu Arg Gln Ala Arg Glu His Ser
        195                 200                 205
```

Glu

<210> SEQ ID NO 4
<211> LENGTH: 627
<212> TYPE: DNA
<213> ORGANISM: Artificial Sequence
<220> FEATURE:
<223> OTHER INFORMATION: 209E-SOD3 DNA

<400> SEQUENCE: 4

```
tggacgggcg aggactcggc ggagcccaac tctgactcgg cggagtggat ccgagacatg    60
tacgccaagg tcacggagat ctggcaggag gtcatgcagc ggcgggacga cgacggcacg   120
ctccacgccg cctgccaggt gcagccgtcg gccacgctgg acgccgcgca gccccgggtg   180
accggcgtcg tcctcttccg gcagcttgcg ccccgcgcca agctcgacgc cttcttcgcc   240
ctggagggct tcccgaccga gccgaacagc tccagccgcg ccatccacgt gcaccagttc   300
ggggacctga gccagggctg cgagtccacc gggcccccact acaacccgct ggccgtgccg   360
cacccgcagc acccgggcga cttcggcaac ttcgcggtcc gcgacggcag cctctggagg   420
taccgcgccg gctggccgc ctcgctcgcg ggcccgcact ccatcgtggg ccgggccgtg   480
gtcgtccacg ctggcgagga cgacctgggc cgcggcggca accaggccag cgtggagaac   540
gggaacgcgg ccggcggct ggcctgctgc gtggtgggcg tgtgcgggcc cgggctctgg   600
gagcgccagg cgcgggagca ctcagag                                       627
```

<210> SEQ ID NO 5
<211> LENGTH: 20
<212> TYPE: DNA
<213> ORGANISM: Artificial Sequence
<220> FEATURE:
<223> OTHER INFORMATION: Foxp3 forward primer

<400> SEQUENCE: 5

```
gcaacagcac tggaaccttc                                                20
```

<210> SEQ ID NO 6
<211> LENGTH: 20
<212> TYPE: DNA
<213> ORGANISM: Artificial Sequence
<220> FEATURE:
<223> OTHER INFORMATION: Foxp3 reverse primer

<400> SEQUENCE: 6

```
gcattgcttg aggctgcgta                                                20
```

<210> SEQ ID NO 7
<211> LENGTH: 20
<212> TYPE: DNA
<213> ORGANISM: Artificial Sequence
<220> FEATURE:
<223> OTHER INFORMATION: T-bet forward primer

<400> SEQUENCE: 7

```
agccagccaa acagagaaga                                                20
```

<210> SEQ ID NO 8
<211> LENGTH: 20
<212> TYPE: DNA
<213> ORGANISM: Artificial Sequence
<220> FEATURE:
<223> OTHER INFORMATION: T-bet reverse primer

<400> SEQUENCE: 8

-continued aatgtgcacc cttcaaaccc					20

<210> SEQ ID NO 9
<211> LENGTH: 20
<212> TYPE: DNA
<213> ORGANISM: Artificial Sequence
<220> FEATURE:
<223> OTHER INFORMATION: GATA3 forward primer

<400> SEQUENCE: 9
acatgtcatc cctgagccac					20

<210> SEQ ID NO 10
<211> LENGTH: 20
<212> TYPE: DNA
<213> ORGANISM: Artificial Sequence
<220> FEATURE:
<223> OTHER INFORMATION: GATA3 reverse primer

<400> SEQUENCE: 10
aggaactctt cgcacacttg					20

<210> SEQ ID NO 11
<211> LENGTH: 18
<212> TYPE: DNA
<213> ORGANISM: Artificial Sequence
<220> FEATURE:
<223> OTHER INFORMATION: RORrt forward primer

<400> SEQUENCE: 11
gcctacaatg ccaccacc					18

<210> SEQ ID NO 12
<211> LENGTH: 18
<212> TYPE: DNA
<213> ORGANISM: Artificial Sequence
<220> FEATURE:
<223> OTHER INFORMATION: RORrt reverse primer

<400> SEQUENCE: 12
attgatgaga accagggc					18

<210> SEQ ID NO 13
<211> LENGTH: 25
<212> TYPE: DNA
<213> ORGANISM: Artificial Sequence
<220> FEATURE:
<223> OTHER INFORMATION: SOD3 forward primer

<400> SEQUENCE: 13
tgttggagca gaggagaagc tcaac					25

<210> SEQ ID NO 14
<211> LENGTH: 24
<212> TYPE: DNA
<213> ORGANISM: Artificial Sequence
<220> FEATURE:
<223> OTHER INFORMATION: SOD3 reverse primer

<400> SEQUENCE: 14
aagctctctt ggagcagctg gaaa					24

<210> SEQ ID NO 15
<211> LENGTH: 20
<212> TYPE: DNA

```
<213> ORGANISM: Artificial Sequence
<220> FEATURE:
<223> OTHER INFORMATION: icIL-1Ra forward primer

<400> SEQUENCE: 15
ttatgggcag cagctcagtt                                                    20

<210> SEQ ID NO 16
<211> LENGTH: 20
<212> TYPE: DNA
<213> ORGANISM: Artificial Sequence
<220> FEATURE:
<223> OTHER INFORMATION: icIL-1Ra reverse primer

<400> SEQUENCE: 16
ttgacacagg acaggcacat                                                    20

<210> SEQ ID NO 17
<211> LENGTH: 21
<212> TYPE: DNA
<213> ORGANISM: Artificial Sequence
<220> FEATURE:
<223> OTHER INFORMATION: sIL-1Ra forward primer

<400> SEQUENCE: 17
tccgcagtca cctaatcact c                                                  21

<210> SEQ ID NO 18
<211> LENGTH: 20
<212> TYPE: DNA
<213> ORGANISM: Artificial Sequence
<220> FEATURE:
<223> OTHER INFORMATION: sIL-1Ra reverse primer

<400> SEQUENCE: 18
ttgacacagg acaggcacat                                                    20

<210> SEQ ID NO 19
<211> LENGTH: 26
<212> TYPE: DNA
<213> ORGANISM: Artificial Sequence
<220> FEATURE:
<223> OTHER INFORMATION: unspliced IL-1Ra forward primer

<400> SEQUENCE: 19
ggcctccgca gtcacctaat cactct                                             26

<210> SEQ ID NO 20
<211> LENGTH: 22
<212> TYPE: DNA
<213> ORGANISM: Artificial Sequence
<220> FEATURE:
<223> OTHER INFORMATION: unspliced IL-1Ra reverse primer

<400> SEQUENCE: 20
ggtcgcacta tccacatctg gg                                                 22

<210> SEQ ID NO 21
<211> LENGTH: 20
<212> TYPE: DNA
<213> ORGANISM: Artificial Sequence
<220> FEATURE:
<223> OTHER INFORMATION: HO-1 forward primer

<400> SEQUENCE: 21
cctggtgtcc cttcaatcat                                                    20
```

```
<210> SEQ ID NO 22
<211> LENGTH: 20
<212> TYPE: DNA
<213> ORGANISM: Artificial Sequence
<220> FEATURE:
<223> OTHER INFORMATION: HO-1 reverse primer

<400> SEQUENCE: 22
ggcgatgagg tggaatacat                                                    20

<210> SEQ ID NO 23
<211> LENGTH: 22
<212> TYPE: DNA
<213> ORGANISM: Artificial Sequence
<220> FEATURE:
<223> OTHER INFORMATION: IDO-1 forward primer

<400> SEQUENCE: 23
tgtgaaccca aaagcattt tc                                                  22

<210> SEQ ID NO 24
<211> LENGTH: 18
<212> TYPE: DNA
<213> ORGANISM: Artificial Sequence
<220> FEATURE:
<223> OTHER INFORMATION: IDO-1 reverse primer

<400> SEQUENCE: 24
aaagacgctg ctttggcc                                                      18

<210> SEQ ID NO 25
<211> LENGTH: 19
<212> TYPE: DNA
<213> ORGANISM: Artificial Sequence
<220> FEATURE:
<223> OTHER INFORMATION: TGF-b forward primer

<400> SEQUENCE: 25
cccagcatct gcaaagctc                                                     19

<210> SEQ ID NO 26
<211> LENGTH: 20
<212> TYPE: DNA
<213> ORGANISM: Artificial Sequence
<220> FEATURE:
<223> OTHER INFORMATION: TGF-b reverse primer

<400> SEQUENCE: 26
gtcaatgtac agctgccgca                                                    20

<210> SEQ ID NO 27
<211> LENGTH: 24
<212> TYPE: DNA
<213> ORGANISM: Artificial Sequence
<220> FEATURE:
<223> OTHER INFORMATION: Galectin-1 forward primer

<400> SEQUENCE: 27
ggtctggtcg ccagcaacct gaat                                               24

<210> SEQ ID NO 28
<211> LENGTH: 20
<212> TYPE: DNA
<213> ORGANISM: Artificial Sequence
<220> FEATURE:
```

```
<223> OTHER INFORMATION: Galectin-1 reverse primer

<400> SEQUENCE: 28
tgaggcggtt ggggaacttg                                                    20

<210> SEQ ID NO 29
<211> LENGTH: 32
<212> TYPE: DNA
<213> ORGANISM: Artificial Sequence
<220> FEATURE:
<223> OTHER INFORMATION: IL-10 forward primer

<400> SEQUENCE: 29
aagctgagaa ccaagaccca gacatcaagg cg                                      32

<210> SEQ ID NO 30
<211> LENGTH: 31
<212> TYPE: DNA
<213> ORGANISM: Artificial Sequence
<220> FEATURE:
<223> OTHER INFORMATION: IL-10 reverse primer

<400> SEQUENCE: 30
agctatccca gagccccaga tccgattttg g                                       31

<210> SEQ ID NO 31
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 31
aaggtcggag tcaacggatt tggt                                               24

<210> SEQ ID NO 32
<211> LENGTH: 24
<212> TYPE: DNA
<213> ORGANISM: Artificial Sequence
<220> FEATURE:
<223> OTHER INFORMATION: GAPDH reverse primer

<400> SEQUENCE: 32
agtgatggca tggactgtgg tcat                                               24
```

COMPOSITION FOR PREVENTING OR TREATING INFLAMMATORY DISEASES, CONTAINING, AS ACTIVE INGREDIENT, STEM CELLS OVEREXPRESSING SOD3

TECHNICAL FIELD

This application claims priority from and the benefit of Korean Patent Application No. 10-2015-0130377 filed on 15 Sep. 2015, the disclosure of which is hereby incorporated herein by reference it its entirety. The present invention relates to a composition comprising, as an active ingredient, stem cells overexpressing extracellular superoxide dismutase (SOD3) for preventing or treating an inflammatory disease and, more specifically, to a pharmaceutical composition comprising, as an active ingredient, stem cells overexpressing SOD3 for preventing or treating an inflammatory disease.

BACKGROUND ART

The inflammatory disease refers to a condition in which edema, redness, and pain, together with the infiltration of immune cells, are shown and histological changes appear in several organs or tissues of the human body due to various external stimulations or internal factors. Such inflammation is triggered by various chemical factors produced from damaged tissues and migrating cells, and these chemical factors are known to vary according to the type of inflammatory process. In normal cases, the living body neutralizes or removes pathogenic factors through inflammatory responses and regenerates damaged tissues to restore normal structures and functions, but if not, the living body proceeds to a diseased state, such as chronic inflammation.

The most common prophylactic or therapeutic agents for treating such inflammatory diseases are largely classified into steroidal and non-steroidal prophylactic or therapeutic agents for inflammatory diseases. Of these, most synthetic prophylactic or therapeutic agents for inflammatory diseases have several side effects as well as main actions, and therefore, there is an urgent need to develop prophylactic or therapeutic agents for inflammatory diseases having excellent efficacy and few side effects.

Mesenchymal stem cells (MSCs) are multi potent progenitor cells having ability to differentiate into mesenchymal tissue lineages. These cells can mediate potential immuno-regulatory effects on various cells by regulating adaptive and innate immune responses, emerging as a novel alternative to treat autoimmune diseases. In addition, these cells are known to have immunosuppressive and anti-inflammatory effects (European Patent No. EP02298861 and US Patent Publication No. US20120269774) and to inhibit the activation and proliferation of T cells (Li Z J et al., *PloS ONE* 8(10): 77159, 2013).

However, only typical anti-inflammatory effects of MSCs are known, and MSC therapeutic agents optimized to have a more potent effect on inflammation-related diseases have not yet been developed. Therefore, there is an urgent need to develop MSC therapeutic agents suitable for the prevention or treatment of inflammatory diseases.

DETAILED DESCRIPTION OF THE INVENTION

Technical Problem

The present inventors, during the research of therapeutic agents for inflammatory diseases, including stem cells suitable for the prevention and treatment of inflammatory diseases while having remarkably few side effects, have found that the overexpression of SOD3 in mesenchymal stem cells (MSCs) significantly enhances immunomodulatory and antioxidative activities, and thus have completed the present invention.

Therefore, an aspect of the present invention is to provide a pharmaceutical composition for preventing or treating an inflammatory disease, the pharmaceutical composition comprising, as an active ingredient, stem cells overexpressing extracellular superoxide dismutase (SOD3).

Another aspect of the present invention is to provide a use of stem cells overexpressing SOD3 for preparing a preparation for treatment of an inflammatory disease.

Still another aspect of the present invention is to provide a method for treating an inflammatory disease, the method being characterized by administering an effective amount of a pharmaceutical composition to a subject in need thereof, the pharmaceutical composition comprising, as an active ingredient, stem cells overexpressing SOD3.

Technical Solution

In accordance with an aspect of the present invention, there is provided a pharmaceutical composition for preventing or treating an inflammatory disease, the pharmaceutical composition comprising, as an active ingredient, stem cells overexpressing extracellular superoxide dismutase (SOD3).

In accordance with another aspect of the present invention, there is provided a use of stem cells overexpressing SOD3 for preparing a preparation for treatment of an inflammatory disease.

In accordance with still another aspect of the present invention is to provide a method for treating an inflammatory disease, the method being characterized by administering an effective amount of a pharmaceutical composition to a subject in need thereof, the pharmaceutical composition comprising, as an active ingredient, stem cells overexpressing SOD3.

Hereinafter, the present invention will be described in detail.

Unless defined otherwise, the technical and scientific terms used herein have the same meaning as commonly understood by one having ordinary skill in the art to which this invention pertains and are consistent with those described in the following literature (Singleton et al, Dictionary of Microbiology and Molecular Biology, 2nd Ed., 1994; Janeway, C., Travers, P., Walport, M., Shlomchik, Immunobiology, 5th Ed., 2001).

The Present Invention Provides a Pharmaceutical Composition for Preventing or Treating an Inflammatory Disease, the Pharmaceutical Composition Comprising, as an Active Ingredient, Stem Cells Overexpressing Extracellular Superoxide Dismutase (SOD3)

The pharmaceutical composition according to the present invention may be a composition comprising SOD3 as an active ingredient, a composition consisting of SOD3 as an active ingredient, or a composition essentially consisting of SOD3 as an active ingredient.

As used herein, the term "comprising" is used synonymously with "including", "containing" or "characterized by", and does not exclude specifically additional, unrecited elements or method steps in the composition and the method according to the present invention. The term "consisting of" excludes additional elements, steps, or ingredients that are not otherwise indicated. The term "essentially consisting of" is meant that in the scope of a composition or method, the term includes described materials or steps as well as any material or step that does not substantially affect basic characteristics thereof.

As used herein, the term "protein" is used interchangeably with the term "polypeptide" or "peptide", and refers to, for example, a polymer of amino acid residues, as typically found in proteins in nature.

The term "SOD3 (superoxide dismutase extracellular)" is an extracellular superoxide dismutase (EC-SOD) protein and refers to an extracellularly secreted protein among three types of superoxide dismutase proteins. The amino acid sequence of human wild-type (WT) SOD3 protein is known by accession number NP_003093.2 and the nucleotide sequence of mRNA encoding human SOD3 protein is known by accession number NM_003102.2 in the NCBI Genbank database.

SOD3 protein catalyzes the dismutation of anions, is present in the extracellular matrix through extracellular secretion, and shows anti-angiogenic, anti-inflammatory, anti-chemotactic, and anticancer effects. Specifically, the SOD3 protein has been known to have useful effects in the treatment of diseases, such as skin cancer, pigmentary disease, photoaging, dermatitis, disorders of epidermal proliferation, psoriasis, atopy, urticaria, and allergy (Korean Patent No. 100676502) and to also have effects in the prevention and treatment of diseases caused by angiogenesis (Korean Patent No. 101019470). Also, the SOD3 protein has been known to have useful effects in the cancer diseases, such as colon cancer, lung cancer, liver cancer, gastric cancer, esophageal cancer, pancreatic cancer, gallbladder cancer, kidney cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, and lymphoma (Korean Patent Publication No. 10-2008-108876.

As used herein, the SOD3 means a protein derived mammals including humans and mice, preferably humans, and may include, most preferably, the amino acid sequence of human wild-type SOD3 protein represented by SEQ ID NO:1, or the amino acid sequence of recombinant SOD3 protein (209E-SOD3) represented by SEQ ID NO: 3.

The human wild-type SOD3 is composed of a signal peptide of from the start amino acid methionine at the N-terminal site to the 18th amino acid alanine, and activated SOD3 consists of 222 amino acids with the signal peptide removed. SOD3 has a heparin binding domain in the C-terminal region (amino acid residues Nos. 210-215). The amino acid sequence of the full-length human SOD3 composed of 240 amino acid residues including the signal peptide is as shown in SEQ ID NO: 1.

In addition, the SOD3 in the present invention may be composed of 209 amino acids obtained by removing, from the full-length human SOD3, the signal peptide at the N-terminal site and 13 amino acids (amino acid residue Nos. 210-222) containing the heparin binding domain of the C-terminal site. The SOD3 protein, from which the signal peptide and the heparin domain have been removed, may be referred to as 209E-SOD3 or 209E, and may have preferably the amino acid sequence represented by SEQ ID NO: 3. The 209E-SOD3 protein may bind with anti-SOD3 antibody, and has been confirmed to have the same enzyme activity and ROS scavenging activity as wild-type SOD3 (Korean Patent Publication No. 10-2008-0108876).

The SOD3 in the present invention includes a functional equivalent, a functional derivative, and a fragment of the SDO3 protein, which have substantially equivalent physiological activity to wild-type SOD3 or 209E-SOD3 protein. The substantially equivalent physiological activity means having the equivalent enzyme activity and/or extracellular secretion and intracellular permeability to wild-type SOD3, and a protein with the substantially equivalent physiological activity, when overexpressed in stem cells, preferably mesenchymal stem cells, enhances immune and inflammation-modulating ability of stem cells due to the equivalent enzyme activity to SOD3. The immune and inflammation-modulating ability of stem cells means, specifically, inhibiting infiltration of immune cells due to inflammation, inhibiting proliferation and differentiation of pro-inflammatory T cells and expression of pro-inflammatory mediators/cytokines, increasing proliferation and differentiation of Treg cells and expression of Treg-related cytokines, and inhibiting phosphorylation of NFkB signaling system, and these are as described in the specification with respect to the characteristics of stem cells overexpressing SOD3 of the present invention.

The functional equivalent of SOD3 may be a polypeptide having sequence homology of at least 70%, preferably at least 80%, and more preferably at least 90% with the amino acid sequence represented by SEQ ID NO: 1 or SEQ ID NO: 3. In addition, the functional equivalent may result from the addition, substitution, or deletion of a portion of the amino acid sequence of SOD3 of the present invention. Here, the substitution of amino acid is preferably a conservative substitution. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). In addition, the functional equivalent includes a variant in which some of the amino acids are deleted from the amino acid sequence of SOD of the present invention. The deletion or substitution of amino acids is preferably located at a region that is not directly associated with the physiological activity of the SOD3 protein. The functional equivalent also includes a variant with addition of several amino acids in both terminal ends of the amino acid sequence of the SOD3 or in the sequence thereof. For example, the functional equivalent may be a peptide in which a portion of the full-length SOD3 has been removed without affecting the enzyme activity of SOD3, such as 209E-SOD3, and may be a polymorphic protein of SOD3, such as small nucleotide polymorphism (SNP) having the substantially equivalent physiological activity to SOD3 protein.

Moreover, the scope of the functional equivalent of the present invention also includes a polypeptide derivative which has a modification of a portion of the chemical structure of the SOD3 protein of the present invention while maintaining the fundamental backbone and physiological activity of the SOD3 protein and physiological activity thereof. Examples of such a modification include, but are not limited to, structural modifications for changing stability, intercellular permeability, storability, volatility, or solubility of the SOD3 protein of the present invention.

The stem cells overexpressing SOD3, contained as an active ingredient in the pharmaceutical composition of the present invention, may be preferably mesenchymal stem cells.

The "mesenchymal stem cell (MSC)" in the present invention refers to a multipotent progenitor cell prior to the differentiation into cells of specific organs, such as bone, cartilage, fat tissue, tendon, nerve tissue, fibroblast, and muscle cell. The mesenchymal stem cells in the present invention are contained in the composition in an undifferentiated state, that is, a state of stem cells. The mesenchymal stem cells of the present invention may be derived from mammals, and preferably humans.

The mesenchymal stem cells of the present invention may be derived from a tissue selected from the group consisting of umbilical cord, umbilical cord blood, placenta, bone marrow, adipose tissue, muscle, amniotic fluid, and amniotic membrane. Preferably, the mesenchymal stem cells of the present invention may be umbilical cord blood or placenta-derived mesenchymal stem cells, and most preferably, may be umbilical cord blood-derived mesenchymal stem cells. The umbilical cord blood or placenta-derived mesenchymal stem cells have excellent differentiation and proliferation abilities compared with bone marrow-derived mesenchymal stem cells.

The term umbilical cord blood used herein refers to the blood collected from the umbilical vein connecting the placenta and fetus in a mammal. The umbilical cord blood can be easily collected from the umbilical vein of a donor at the time of birth. More specifically, in the case of normal vaginal delivery, the umbilical cord blood can be collected from the umbilical vein, which has been expelled out of the uterus while the placenta still remains in the uterus. In addition, in the case of cesarean section, the umbilical cord blood is collected from the umbilical vein while the placenta has also been expelled out the uterus after birth.

As used herein, the term "placental stem cells" refers to stem cells or progenitor cells derived from the mammalian placenta regardless of the shape, cell surface markers, or number of passages after primary culture, and the placental stem cells are cells adhering to a tissue culture substrate, for example, a tissue culture plastic or fibronectin coated tissue culture plate. However, the term "placental stem cells" used herein does not refer to trophoblasts. If cells have at least one of the features of stem cells, for example, the ability to differentiate into at least one cell type, such cells are stem cells.

Mesenchymal stem cells may be isolated from the placenta or umbilical cord blood by a method known in the art. The mesenchymal stem cells may be isolated by any isolation method known in the art. Examples of such a method include density gradient fractionation, immunoselection, and differential adhesion separation. The isolation and culture of mesenchymal stem cells from the umbilical cord blood or placenta can be carried out by any method that has been used in the conventional art.

The culture of the isolated mesenchymal stem cells may be carried out in a cell culture medium known in the art, and examples of the cell culture medium may include, but are not limited to, DMEM medium, McCoys 5A medium, Eagle's basal medium, CMRL medium, Glasgow minimum essential medium, Ham's F-12 medium, Iscove's modified Dulbecco's medium, Leibovitz's L-15 medium, RPMI 1640 medium, KSB-3 basal medium. In the present invention, one or more auxiliary ingredients may be added to the cell culture medium as needed, and antibiotic and antifungal agents for preventing the contamination of microorganisms, including fetal bovine serum and sera of horse or human, may be used.

The isolated or cultured stem cells may be stored by any method known in the art before use. In general, stem cells may be freeze-stored after cryoprotection treatment. The cryoprotection treatment may be carried out using a cytoprotective agent, such as DMSO, glycerol, polyvinylpyrrolidone, polyethylene glycol, albumin, dextran, sucrose, ethylene glycol, i-erythritol, D-ribitol, D-mannitol, D-sorbitol, i-inositol, D-lactose, or choline chloride, and these cytoprotective agents are known in the art.

The stem cells overexpressing SOD3 according to the present invention may be obtained by transfecting stem cells with a recombinant expression vector comprising a polynucleotide encoding SOD3.

As used herein, the term "expression" means the production of proteins or nucleic acids in cells, and the term "overexpression" means an excessive increase in the expression level of a particular gene compared with a normal state or a general state. In the present invention, the stem cells overexpressing SOD3 are specially stem cells, of which the expression level of the SOD3 protein is increased and thus the activity of SOD3 protein is increased.

As used herein, the term "polynucleotide" or "nucleic acid" refers to single or double-stranded deoxyribonucleotide (DNA) or ribonucleotide (RNA). Unless otherwise limited, the term includes known analogs of naturally occurring nucleotides that hybridize with nucleic acids in a manner similar to naturally occurring nucleotides.

The most common method of SOD overexpression in stem cells is to increase the copy number of SOD3 gene by artificially or experimentally introducing a polynucleotide comprising SOD3 gene into stem cells. The injection of an exogenous polynucleotide, which is not originally retained by cells, into the cells is called transfection, and as a result, the change of genetic traits of the cells is called transformation. The procedure in which the exogenous polynucleotide is injected into the cells through a virus or virus-derived vector is called transduction. As used herein, the terms "transformation", "transfection", and "transduction" refer to having different genetic traits from the wild-type by the introduction of an exogenous polynucleotide into cells or such a procedure, and these terms are used with similar meanings.

In the present invention, the polynucleotide encoding SOD3 may be SOD3 gene derived from mammals, and preferably may include the nucleotide sequence encoding human wild-type SOD3 and represented by SEQ ID NO: 2, or the nucleotide sequence encoding 209E-SOD3 and represented by SEQ ID NO: 4.

In addition, the polynucleotide encoding SOD3 includes the nucleotide sequence of human SOD3, preferably a sequence that shows substantial identity with the nucleotide sequence represented by SEQ ID NO: 2 or SEQ ID NO: 4. The substantial identity means having at least 70% sequence homology when the polynucleotide encoding human SOD3 and any other nucleotide sequence as a comparative target are aligned as much as possible and then compared and analyzed using analysis methods and algorithms that are commonly used in the art. The protein encoded by a nucleotide sequence, which is substantially homologous to the polynucleotide encoding SOD3 may be SOD3 protein or preferably a functional equivalent of a protein including the amino acid sequence represented by SEQ ID NO: 1 or SEQ ID NO: 3. The functional equivalents of the SOD3 protein are as described above in the specification.

As used herein, the term "recombinant expression vector" refers to a vector capable of expressing a target protein or a target nucleic acid (RNA) in suitable host cells, and indicates a gene construct containing an essential regulatory element operatively linked so as to express a polynucleotide (gene) insert. The term "operatively linked" refers to the functional linkage of a nucleic acid expression regulatory sequence and a nucleic acid sequence encoding a target protein or RNA so as to perform general functions. That is, the term means that a nucleic acid sequence encoding a protein or RNA is linked in such a manner that gene expression is enabled by an expression regulatory sequence, and for example, a promoter should be operatively linked to a nucleic acid sequence encoding a protein or RNA to affect the expression of the coding nucleic acid sequence. The operative linkage with a recombinant vector may be carried out by using a gene recombinant technique that is well known in the art, and site-specific DNA cleavage and linkage are carried out using an enzyme that is generally known in the art.

The recombinant expression vector of the present invention is not particularly limited to a kind thereof so long as the vector is commonly used in a cloning field, and examples of the recombinant expression vector include, but are not limited to, a plasmid vector, a cosmid vector, a bacteriophage vector, and a virus vector. Preferably, a virus-derived vector may be used. Examples of the plasmid may include *Escherichia coli*-derived plasmids (pBR322, pBR325, pUC118, pUC119, and pET-22b (+)), *Bacillus subtilis*-derived plasmids (pUB110 and pTP5), and yeast-derived plasmids (YEp13, YEp24, and YCp50). Examples of the virus may include: animal viruses, such as retrovirus, adenovirus, and vaccinia virus; and insect viruses, such as baculovirus, but are not limited thereto.

The expression vector comprising a nucleic acid according to the present invention may be introduced into stem cells by a method known in the art, for example, but is not limited to, transient transfection, microinjection, transduction, cell fusion, calcium phosphate precipitation, liposome-mediated transfection, DEAE dextran-mediated transfection, polybrene-mediated transfection, electroporation, gene gun, and a known method for injecting a nucleic acid into cells.

The stem cells overexpressing SOD3 according to the present invention may be stem cells transfected by injecting a recombinant expression vector comprising a polynucleotide encoding SOD3 into mesenchymal stem cells using electroporation or virus-mediated transfection.

In addition, the stem cells of the present invention may be prepared by the following steps using a recombinant virus vector: (a) preparing a recombinant virus vector comprising a DNA construct in which a shuttle vector, a nucleic acid encoding SOD3 and/or a protein transfection domain are operatively linked; (b) preparing an SOD3 expression recombinant virus by transfecting the recombinant virus vector into a virus-producing cell line; and (c) infecting mesenchymal stem cells with the SOD3 expression recombinant virus.

Examples of the shuttle vector include PUB110, PGX1416, PGX1417, PUL61, PSA77, and PGX1418. In an example of the present invention, pCA14 (Invitrogen) of ColE1 was used. The virus vector of the present invention is selected from the group consisting of a retrovirus vector, an adenovirus vector, an adeno-associated virus (AAV) vector, a vaccinia virus vector, a herpes virus vector, a lentivirus vector, and an avipox virus vector. The virus vector of the present invention may be preferably an adenovirus vector.

The mesenchymal stem cells (MSCs) transfected by SOD3 to overexpress SOD3 according to the present invention has increased expressions of genes having immunosuppressive functions, and exerts potent immunomodulatory ability by regulating the functions and infiltration of neutrophils and dendritic cells in inflammatory responses. Also, it was confirmed that MSCs overexpressing SOD3 remarkably reduced the expressions of pro-inflammatory mediators/cytokines, especially, inhibited the activation of TRL-7 and NFkB. Examples of the present invention suggest that MSCs overexpressing SOD3 can be an effective therapeutic agent for an inflammatory disease.

The stem cells overexpressing SOD3 of the present invention has at least one of the following properties:

(a) inhibiting the infiltration of at least one selected from the group consisting of $CD4^+$ T cells, $CD8^+$ T cells, neutrophils, and dendritic cells;

(b) inhibiting the differentiation and proliferation of $CD4^+$ T cells, $CD8^+$ T cells, Th1 cells, Th2 cells, and Th17 cells and promoting the differentiation and proliferation of Treg;

(c) inhibiting the expression of at least one inflammatory cytokine selected from the group consisting of IL-1α, IL-1β, IL-4, IL-6, IL-17, IL-20, IL-22, IL-23, TNF-α, IFN-γ, CXCL1, and CCL20 but increasing the expressions of IL-10 and TGF-β, which are Treg-related cytokines;

(d) inhibiting the phosphorylation of at least one selected from the group consisting of NFkB, p38, JNK, STAT1, and STAT3;

(e) increasing the in vivo cAMP level; and (f) increasing the expression of genes having immunosuppressive functions, such as icIL-1Ra, TGF-β, IL-10, HO-1, and IDO-1.

The immunoregulatory abilities of stem cells overexpressing SOD3, especially mesenchymal stem cells (MSC), which have been revealed through various cell experiments and animal experiments by the present inventors, are specifically as follows.

In an example of the present invention, it was observed that the expression level of pro-inflammatory cytokines induced by TNF-α and IFN-γ stimulation were remarkably reduced whereas the expression of TGF-β known as an inflammatory cytokine was increased in HaCaT cells co-culture with SOD3-transfected MSCs (SOD3-MSC) compared with HaCaT cells co-cultured with untransfected MSCs.

in another example, it was confirmed that the expression levels of various genes having immunosuppressive functions, such as icIL-1Ra, IL-10, HO-1, and IDO-1, were significantly increased in SOD3-MSCs compared with untransfected MSCs or, as a control, LacZ-transfected MSCs (LacZ-MSC). These results indicate that the immunoregulatory ability was greatly enhanced in MSCs overexpressing SOD3 compared with MSCs not-overexpressing SOD3. It has been especially that HO- and IDO-1 have immunomodulatory activity, such as inhibiting reactions by inflammatory cytokines and Th17 and inducing apoptosis of immune cells. Therefore, it can be understood that MSCs overexpressing SOD3 can effectively regulate inflammation and transplant rejection, which may occur in patients with autoimmune diseases, such as asthma, psoriasis, and atopy, and transplant patients, through increased expression of HO-1 or IDO-1.

In another example of the present invention, it was confirmed that, in the mixed lymphocyte reaction experiments with co-culture with MSCs, the differentiation and proliferation of $CD4^+$ T cells and $CD8+^+$ T cells were inhibited in the co-culture with SOD3-MSCs compared with the co-culture with untransfected MSCs. In addition, in another example of the present invention, it was further confirmed that, as a result of inducing the differentiation of undifferentiated T cells into Th1, Th2, Th17, and Treg cells while co-culturing the undifferentiated T cells with respective different types of MSCs (MSC, LacZ-MSC, SOD3-MSC, and MSC+DETCA), SOD3-MSCs promoted the differentiation of undifferentiated T cells into Treg cells and inhibited the differentiation of undifferentiated T cells into Th17 cells and other T cells compared with MSC not-overexpressing SODS.

In another example of the present invention, mouse experiments were conducted using models of acute and aggressive dermatitis, such as psoriasis, among inflammatory diseases. The lesions of chronic and acute dermatitis, which were determined by skin symptoms such as erythema and scaling, dermal thickness, and infiltration of immune cells into skin, were more effectively improved in mice administered with SOD3-MSCs rather than mice administered with MSCs. Similar to the results confirmed in the cellular experiments, it was also confirmed that the expressions of pro-inflammatory mediators were more effectively inhibited and the expression of IL-10 associated with Treg cells was increased in mice administered with SOD3-MSCs. It was additionally confirmed that the NFkB signaling system was especially inhibited in signaling pathway experiments.

It was also confirmed that, in mouse models of atopy-like dermatitis induced by ovalbumin, the inflammatory lesions were remarkably alleviated in mice administered with SOD3-MSCs rather than mice administered with MSCs.

The above cellular and animal experiment results indicate that the immunoregulatory ability of MSCs was remarkably enhanced due to the overexpression of SOD3, suggesting that MSCs overexpressing SOD3 can be used as a more effective stem cell therapeutic agent rather than an existing non-treated MSCs in the prevention or treatment of inflammatory diseases.

As used herein, the term "treatment" means a clinical procedure intended to alter a natural course of an individual or cell to be treated, and may also be performed for the prevention of clinical pathology. Preferable effects of the treatment include suppressing occurrence or recurrence of diseases, alleviating symptoms, reducing direct or indirect pathological consequences of diseases, reducing disease progression rates, improving, bettering, or relieving disease conditions, or improving prognosis.

As used herein, the term "prevention" refers to all actions that suppress the onset of diseases or delays the progress of disease.

The inflammatory disease, which is the target of the prevention or treatment in the present invention, may be preferably a Th2 or Th17-mediated disease. The "Th2 or Th17-mediated disease" refers to a disease mediated by Th2 cells or Th17 cells. The Th2 or Th17-mediated disease in the present invention may be preferably selected from the group consisting of a transplant rejection, an autoimmune disease, an inflammatory bowel disease, an inflammatory eye disease, an inflammatory skin disease, and an allergic disease.

The Th2-mediated disease refers to a disease mediated by Th2 cells, and means a disease caused by the production and activity of allergen-specific Th2 cells causing allergy. Th2 cells are immune cells that express CD4 and T cell receptor (TCR), and are involved in humoral immunity while secreting cytokines, such as IL-4, IL-5, IL-6, and IL-13 through the actions of GATA3 transcription factors. The overactivation of Th2 cells against autoantigen has been reported to result in mast cell and IgE-involved allergies and hyperimmune responses. It can be seen that Th2-mediated diseases including atopic dermatitis, other skin diseases associated with atopy, allergic rhinitis, and allergic asthma can be treated by inhibiting the differentiation or activation of Th2.

The Th17-mediated disease refers to a disease, which is caused or worsened by an imbalance between Th17/Treg cells due to the excessive differentiation of Th17 cells or excessive activity of Th17 cells. Th17 cells, which are representative pro-inflammatory cells, differentiate through the actions of transcription factors, such as RORγt and STAT-3, when naïve $CD4^+$ T cells undergo antigenic stimulations in the presence of TGF and IL-6. The mature Th17 cells secrete inflammatory cytokines IL-17, IL-21, IL-22, and the like, and infiltrate into inflamed peripheral tissues to interact with macrophages, dendritic cells, fibroblasts, vascular endothelial cells, osteoclasts, and the like, thereby amplifying the secretion of inflammatory cytokines and other inflammatory factors and causing tissue damage. These Th17 cells have revealed to be major pathogenic cells in various autoimmune diseases, allergic diseases, inflammatory diseases, and transplant rejections. Contrary to Th17 cells, Treg cells are cells functioning to regulate inflammation, and naïve CDC T cell differentiate with the expression of transcription factors, such as Foxp3, when receiving proper antigenic stimulation in the presence of TGFβ. The mature Treg cells are known to reduce the proliferation and activity of T cells through cytokines, such as TGFβ and IL-10.

The Treg cells, especially, play an important role in self-tolerance in the immune system, and the possibility of treating autoimmune diseases and transplant rejections by regulating Treg activity has been suggested in animal experiments using mouse models or the like.

The Treg cells and Th17 cells have opposite functions of suppressing inflammation or amplifying inflammation, respectively. However, these cells are differentiated from the same progenitor cells, and balanced in a healthy normal state. The direction of differentiation into Treg or Th17 cells is determined depending on the kind of inflammatory cytokine that is present when naïve $CD4^+$ T cells differentiate by TGF and antigenic stimulation, and Th17-mediated diseases are caused when the balance between Treg cells and Th17 cells, which should properly control each other, is broken due to excessive differentiation or activity of pathogenic Th17 cells. Therefore, it can be seen that Th17-mediated diseases can be treated by inhibiting the proliferation and differentiation of Th17 cells and inducing the differentiation of Treg cells to restore the balance and homeostasis between the immune cells.

The present inventors have confirmed in the examples through the cellular and animal experiments that MSCs transfected to overexpress SOD3 (SOD3-MSCs) inhibited the differentiation of Th2 and Th1 cells and increased the differentiation of Treg cells. It was confirmed that, in particular T cell differentiation conditions, the expression levels of Th2 markers, such as IL-4 and GATA3, and Th17 markers, such as RORγt and IL-17, were remarkably reduced and on the contrary, the expression levels of Treg markers, such as Foxp3, TGFβ, and IL-10, were greatly increased in naïve $CD4^+$ T cells co-cultured with SOD3-MSCs compared with a control not-co-cultured with MSCs or T cells co-cultured with MSCs not-overexpressing SOD3, and thus SOD3-MSCs inhibited the differentiation of Th2 and Th17 cells and promoted the differentiation of Treg cells (example <1-7>). In addition, it was observed that, also in the chronic and aggressive dermatitis mouse models, the expression levels of Th2 and Th17-related pro-inflammatory cytokines, such as IL-6, IL-17, and IL-22, were remarkably reduced and on the contrary, the expression of Treg-related inflammation regulatory cytokine IL-10 was significantly increased in the skin of mice injected with SOD3-MSCs compared with MSCs not-overexpressing SOD3 (example <2-3>). In the aggressive dermatitis mouse models and atopy-like dermatitis mouse models, SOD3-MSCs had an excellent effect on the alleviation of symptoms than MSCs not-overexpressing SOD3. The above experiment results suggest that MSCs overexpressing SOD3 can be a cell therapeutic agent effective for Th2 or Th17-mediaed diseases.

More specifically, the inflammatory disease may be one or more disease selected from the group consisting of acute or chronic transplant rejection, graft versus host disease, inflammatory bowel disease, Crohn's disease, ulcerative colitis, inflammatory skin disease, multiple sclerosis, pancreatitis, traumatic shock, bronchial asthma, allergic rhinitis, allergic conjunctivitis, cystic fibrosis, acute bronchitis, chronic bronchitis, acute bronchiolitis, chronic bronchiolitis, osteoarthritis, gout, spondyloarthropathies, ankylosing spondylitis, Reiter's syndrome, psoriatic arthropathy, bowel disease spondylitis, juvenile arthropathy, juvenile ankylosing spondylitis, reactive arthropathy, infectious arthritis, post-infectious arthritis, Lou Gehrig's disease, nodular polyarteritis, hypersensitive vasculitis, Lou Gehrig's granulomatosis, polymyalgia rheumatica, joint cell arteritis, calcium pyrophosphate deposition arthropathy, pseudo gout, nonarticular rheumatism, bursitis, tendovaginitis, epicondylitis, neuropathic joint disease or charcot joint, hemarthrosis, allergic purpura, hypertrophic osteoarthropathy, multicentric reticulohistiocytoma, scoliosis, hemochromatosis, hemoglobinopathy, hyperlipoproteinema, hypogammaglobulinemia, familial Mediterranean fever, Behcet's disease, systemic lupus erythematosus, relapsing fever, multiple sclerosis, septicemia, septic shock, acute respiratory distress syndrome, multiorgan dysfunction syndrome, chronic obstructive pulmonary disease, rheumatoid arthritis, acute lung injury, broncho-pulmonary dysplasia, type 1 diabetes, type 2 diabetes, arteriosclerosis, Alzheimer's dementia, familial cold autoinflammatory syndrome, Muckle-Wells syndrome, neonatal multisystem inflammatory disease, chronic infantile neurologic cutaneous articular syndrome, adult-onset Still's disease, contact dermatitis, hydatidiform mole, syndrome of pyogenic arthritis, pyoderma gangrenosum and acne (PAPA syndrome), hyperimmunoglobulin D syndrome, cryopyrin-associated periodic syndrome, keratitis, conjunctivitis, retinitis, retinal vasculitis, uveitis, eyeliditis, allergic conjunctivitis, dry eye, progressive systemic sclerosis, polymyositis, autoimmune encephalomyelitis, myasthenia gravis, polyarteritis *nodosa*, and fibromyalgia syndrome.

As used herein, the "transplant rejection" may be specifically an acute or chronic transplant rejection resulting from apoptosis and tissue necrosis caused by the infiltration and attack of in vivo immune cells into transplant organs of transplant patients after the transplant of solid organs, such as heart, lung, heart and lung complex, liver, kidney, pancreas, skin, bowel, or cornea, and may be graft-versus-host disease (GVHD) after the transplant of bone marrow.

Of the inflammatory diseases, the inflammatory skin disease is one or more disease selected from the group consisting of psoriasis, atopic dermatitis, eczematous dermatitis, contact dermatitis, seborrheic dermatitis, *pityriasis rosea*, squamous cellulitis, vasculitis, *pityriasis rubra pilaris*, cellulitis, folliculitis, carbuncle, pemphigus, bullous pemphigus, epidermolysis bullosa, urticaria, angioedema, vasculitis, erythema, and cutaneous eosinophilia.

In addition, the pharmaceutical composition comprising, as an active ingredient, stem cells overexpressing SOD3 of the present invention may further contain a pharmaceutically acceptable carrier and diluent. The pharmaceutically acceptable carrier and diluent may be biologically and physiologically compatible with recipients receiving the same. Examples of the pharmaceutically acceptable diluent may be, but are not limited to, saline, aqueous buffers, solvents and/or dispersion media.

Furthermore, the present invention provides a pharmaceutical composition comprising, as an active ingredient, stem cells overexpressing SOD3 for preventing or treating an autoimmune disease or transplant rejection.

As described above, pro-inflammatory Th17 cells are commonly involved in autoimmune diseases or transplant rejection, and according to the establishment by the present inventors, MSCs overexpressing SOD3 inhibit the proliferation and differentiation of Th17 cells and promote the differentiation of Treg cells regulating inflammation. In addition, it was confirmed that the expression levels of various genes having immunosuppressive functions, such as icIL-1Ra, TGF-$\beta$, IL-10, HO-1, and IDO-1, were greatly increased and the immunoregulatory ability to inhibit hyperimmune responses was greatly enhanced in MSCs overexpressing SOD3. Therefore, a person skilled in the art can expect effects in the prevention or treatment of autoimmune diseases and transplant rejections by inhibiting hyperimmune responses through the pharmaceutical composition comprising, as an active ingredient, stem cells overexpressing SOD3 according to the present invention.

The "transplant rejection", as described above, may be an acute or chronic transplant rejection occurring in transplant patients after the transplant of solid organs, such as heart, lung, heart and lung complex, liver, and may be graft-versus-host disease (GVHD) occurring in transplant patients after the transplant of bone marrow.

In addition, the "autoimmune disease" refers to a disease that occurs by a body immune system attacking internal normal cells or proteins but not antigens derived from the outside, and specific examples of the autoimmune disease include systemic lupus erythematosus, lupus, rheumatoid arthritis, autoimmune hepatitis, autoimmune hemolytic disease, drug-induced autoimmune hemolytic anemia, autoimmune inner ear disease, Meniere's disease, type 1 diabetes, lupus, Behcet's disease, Crohn's disease, Guillain-Barre syndrome, autoimmune thyroiditis, Hashimoto's thyroiditis, ulcerative colitis, Sjogren's syndrome, scleroderma, multiple sclerosis, nodular polyarteritis, psoriasis, atopic dermatitis, albumin, Pemphigus vulgaris, dermatomyositis, myasthenia gravis, and Addison's disease.

The transplant rejections and autoimmune diseases both are often accompanied by hyper-inflammatory responses, and thus are also classified as inflammatory diseases, and therefore, some of the diseases described herein as inflammatory diseases may belong thereto.

In addition, the pharmaceutical composition of the present invention may be formulated by a method known in the art so as to provide rapid, sustained, or delayed release of an active ingredient after the pharmaceutical composition is administered to mammals.

The pharmaceutical composition of the present invention is preferably formulated in the form of an injection. Examples of administration routes may include, but are not limited to, transdermal, intramuscular, intraperitoneal, intravenous, subcutaneous, intranasal, intrathecal, and intraoral routes. In an example of the present invention, mice were administered with SOD3-transfected MSCs through subcutaneous injection to investigate the therapeutic effect.

In addition, the pharmaceutical composition of the present invention may be applied using catheterization, and according to a peripheral vein approach, cells can be injected through a catheter with a single lump or several smaller aliquots. Examples of the administration of cells using a catheter may include standard peripheral venous catheterization, central venous catheterization, or intravenous delivery through pulmonary catheterization.

An effective dose of the pharmaceutical composition of the present invention may be properly determined according to the foregoing particular uses by a person skilled in the art considering various factors, such as the route of administration, the time of administration, the number of times of treatment, the period of treatment, and patient's age, weight, health condition, sex, severity of disease, susceptibility to drugs, diet, and excretion rate. As used herein, the term "effective amount" refers to an amount sufficient to exhibit an effect of alleviation, treatment, prevention, detection, or diagnosis of inflammatory diseases, autoimmune diseases, or transplant rejections when administered to a subject, and the term "subject" may be an animal, preferably a mammal, most preferably an animal including a human, and may be cells, tissues, organs, or the like derived from an animal. The subject may be a patient in need of treatment.

The method of the present invention may employ stem cells in an amount as needed in order to inhibit inflammation responses. For examples, the stem cells may include $1\times10^2$, $1\times10^5$, $1\times10^7$, $1\times10^8$, $1\times10^9$, or more stem cells. In an example of the present invention, $2\times10^6$ SOD3-transfected MSCs were subcutaneously injected into mouse models.

The administration may be performed once a day or divided into several times. The pharmaceutical composition of the present invention may be administered alone or co-administered with another therapeutic agent known to have effects in the prevention or treatment of inflammatory diseases, autoimmune diseases, and transplant rejections. In the case of the co-administration, the pharmaceutical composition and another therapeutic agent may be administered sequentially or simultaneously. In the administration alone or co-administration, the pharmaceutical composition of the present invention is preferably administered in an amount such that the maximum effect can be obtained in a minimal amount without side effects, and such an amount can be easily determined by a person skilled in the art.

Furthermore, the present invention provides a use of stem cells overexpressing SOD3 for preparing a preparation for treatment of an inflammatory disease.

As for the above use, the inflammation-modulating activity of the stem cells overexpressing SOD3 of the present invention, especially, mesenchymal stem cells (MSCs) overexpressing SOD3, therapeutic effects of inflammation diseases on the basis of inflammation-modulating activity, and the manufacturing method for stem cells overexpressing SOD3 are as described in the specification.

Furthermore, the present invention provides a method for treating an inflammatory disease, the method being characterized by administering an effective amount of a pharmaceutical composition comprising, as an active ingredient, stem cells overexpressing SOD3 to a subject in need thereof.

The pharmaceutical composition according to the present invention may be a composition comprising SOD3 as an active ingredient, a composition consisting of SOD3 as an active ingredient, or a composition essentially consisting of SOD3 as an active ingredient.

As for the method for treating an inflammatory disease, the inflammation-modulating activity of the stem cells overexpressing SOD3 according to the present invention, especially, mesenchymal stem cells (MSCs) overexpressing SOD3, therapeutic effects of inflammation diseases on the basis of inflammation-modulating activity, and the effective amount and the administration manner to exhibit therapeutic effects may be referred to in the specification.

Advantageous Effects

Accordingly, the present invention provides a composition comprising, as an active ingredient, stem cells overexpressing SOD3 for preventing or treating an inflammatory disease. The mesenchymal stem cells (MSCs) transfected by SOD3 to overexpress SOD3 have more potent antioxidative activity and immunomodulatory functions compared with general MSCs, and therefore, SOD3-transinduced MSCs can be an effective therapeutic agent for an inflammation disease, an autoimmune disease, or a transplant rejection.

Mode For Carrying Out The Invention

Figure 1:
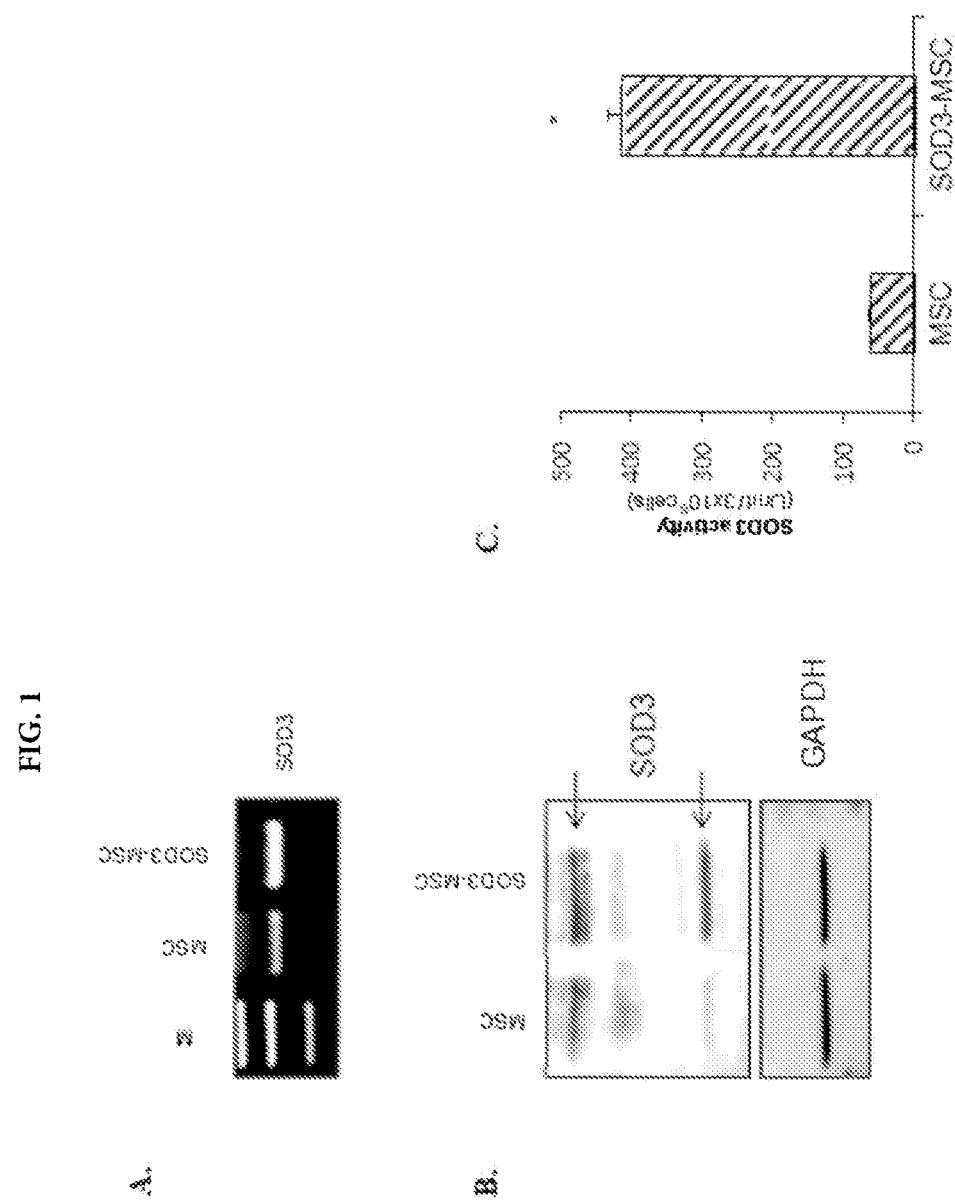
FIG. 1 shows the experiment results of RT-PCR (FIG. 1A), western blot (FIG. 1B) and SOD3 activity (FIG. 1C) to investigate expression patterns of SOD3 in SOD3-transfected MSCs (SOD3-MSC) or control MSCs (MSC).

Hereinafter, the present invention will be described in detail.

However, the following examples are merely for illustrating the present invention and are not intended to limit the scope of the present invention.

<Methods>

Culture and Identification of MSCs

Human umbilical cord blood derived mesenchymal stem cells (hUCB-MSCs) were collected from blood samples of human umbilical cord with the consent of donors. The blood samples of umbilical cord were stored in a blood collection bag containing citrate phosphate glucose as an anti-coagulant. Treatments for experiments were conducted within 24 hours. A fraction of the mononuclear cells was separated by centrifugation in a Ficoll-Paque PLUS gradient (Amersham Biosciences). The fraction was washed with HBSS (Jeil Biotech Services), and resuspended in low-glucose Dulbecco's modified Eagle's medium (DMEM, Invitrogen Corp), 20% fetal bovine serum (Gibco-BRL), 2 mM L-glutamine, 1 mM sodium pyruvate, and 1% antibiotic/antimycotic (Life Technologies). The antibiotic/antimycotic contains 100 U/ml penicillin, 100 µg/ml streptomycin, and 25 µg/ml amphotericin B. After 7 days, non-adherent cells were discarded, and adherent cells were cultured with two medium changes per week. Cells were maintained at 37E in a humidified atmosphere containing 5% $CO_2$. Approximately 60% of the confluent cells were detached with 0.1% trypsin-EDTA and re-plated in culture flasks.

The immunophenotypes of the hUCB-MSC were assessed for the presence of positive markers for MSC-related antigens and the absence of markers for hematopoietic lineage markers by flow cytometry (Epics XL, Beckman Coulter). The positive markers include CD90 (Thy-1), CD105 (endoglin), and SH3 (CD73), and the hematopoietic lineage markers include CD34 and CD45 and endothelial markers such as CD31. The cells were positive for HLA class I but negative for HLA-DR. The respective fluorescent conjugated monoclonal antibodies were obtained from Becton Dickinson.

Confirmation of SOD3 Transfection and SOD3 Overexpression Using Electroporation

The experimental results in FIGS. 1 to 4 were obtained by using SOD3-transfected MSCs by electroporation. For electroporation, electrical stimulation (1000 voltage, 1 pulse) was applied to MSCs according to the Neon™ protocol (Invitrogen) to increase the permeability of cell membranes and inject DNA into cells, and the presence or absence of DNA overexpression was determined by obtaining proteins, followed by western blotting or by amplifying the human SOD3 gene (Genbank accession number NM 003102.2) by PCR, followed by identification on the 5% agarose gel. The amplification program consisted of 94 =5 min; 94☐40 s, 57☐30 s, 72☐60 s (35 cycle); 72☐10 min; and 4☐ 0–∞ (∞ is infinite, meaning that there is no specified time).

Adenovirus Expression Vector an Transfection Conditions for SOD3 Transfection

The experimental results in FIGS. 5 to 21 were obtained by using SOD3-transfected MSCs by electroporation. pRC/CMV hSOD3 vector containing human SOD3 was inserted into E1 shuttle vector pCA14 by homologous recombination. Merge shuttle vector and vector dE1-k35/LacZ were integrated again by homologous recombination to generate the final construct dE1-k35/SOD3. Supernatants containing recombinant adenoviruses were separated from plaque and amplified on 293 cells. Mesenchymal stem cells (MSCs) were then transfected with prepared adenoviral human SOD3 and control LacZ at 10 multiplicity of infection (MOI).

SOD3 Activity Measurement

The enzyme activity of SOD3 was confirmed by measuring superoxide radicals. 200M xanthine (Sigma) and 50M WST-1 (Dojindo) in PBS were mixed with 20 µl of sample, followed by treatment with 0.0005 units of XOD (Sigma), and then the formazan dye signal development was spectroscopically measured.

MTT Assay

MTT assay was conducted to measure the cell proliferation of MSCs (Man et al., 2006; Weichert et al., 1991). $6 \times 10^3$ MSCs were incubated for 24 hours, and the cultured MSCs were transfected with human SOD3 gene using electroporation, and at 24 hours, 48 hours, and 72 hours, corresponding wells were treated with 20 µl of MTT (5 mg/ml), and further incubated for 4 hours. Medium was removed, and the cells were lysed with 100 µl of dimethyl sulfoxide per well, and the absorbance was measured using absorption wavelength of 595 nm (Bio-Tek Instruments, Winooski, Vt., USA).

Measurement of Reactive Oxygen Species Generated in MSCs by TNF-α and IFN-γ Stimulations MSCs were dispensed on 6-well plates and incubated for 24 hours, and then stimulated with 10 ng/ml TNF-α and 100 U/ml IFN-γ for 1 hour. The cells were stabilized with Hanks balanced salt solution (HBSS) for 30 minutes, and then stained with 10 µM 2,7-dichlorofluorescin diacetate (H2DCF-DA) at 37☐ for 30 minutes. ROS was observed by a confocal microscope at an emission wavelength of 513 nm and an excitation wavelength of 488 nm through DCF-fluorescence, and fluorescence was measured by a fluorescence spectrophotometer (Synergy, BIOTEK, US).

Immunosuppressive Molecule Expression Analysis

For analysis of the expression of genes with immunosuppressive functions expressed in MSCs, MSCs were incubated by the following method, and the gene expression was analyzed in the presence or absence of stimulations with TNF-α and IFN-γ:

Day 0: MSCs ($1\times10^4$ cells/cm$^2$) were incubated on a 60-mm culture dish (medium volume: 3 ml) and cells were incubated to 70-80% confluency.

Day 1: The incubated MSCs were transfected with SOD3 by the infection with adenovirus containing wild-type SOD3 or a control virus (AdLacZ) for 24 hours.

Day 2: The medium was exchanged with new MSC growth medium 24 h after viral infection.

Day 3: After additional incubation for 24 hours, TNF-α (10 ng/ml) and IFN-γ (100 Unit/ml) were added to obtain stimulated or unstimulated cells, and the corresponding gene expressions were analyzed by the measurement of mRNA levels.

For gene expression analysis, cDNA was synthesized from 1 μl of total RNA using QuantiTect Reverse Transcription Kit (QIAGEN). Briefly, genomic DNA was removed from template RNA using gDNA wipeout buffer, incubated at 42E for 2 m, and immediately stored on ice. Thereafter, the reverse transcriptase, RT buffer, and RT primer mix were mixed with the template RNA, and the reaction was carried out at 42☐ for 15 m and at 95☐ for 3 m. The synthesized cDNA was stored at −20 ☐ before use. Then, 0.25 template, 1 μl of corresponding primers, 10 μl of TOP polymerase mixture, and 8.75 μl of distilled water were mixed, and RT-PCR was performed in a final volume of 20 μl. The PCR results were confirmed by electrophoresis on 1% agarose gel. The primer sequences used for RT-PCR and real-time PCR were as follows, and were customized by Bioneer (Korea): icIL-1Ra forward 5'-TTATGGGCAGCAGCTCAGTT-3'(SEQ ID NO: 15), reverse 5'-TTGACACAGGACAGGCACAT-3'(SEQ ID NO: 16); sIL-1Ra forward 5'-TCCGCAGTCACCTAAT-CACTC-3'(SEQ ID NO: 17), reverse 5'-TTGACACAGGACAGGCACAT-3'(SEQ ID NO: 18); unspliced IL-1Ra forward 5'-GGCCTCCGCAGT-CACCTAATCACTCT-3'(SEQ ID NO: 19), reverse 5'-GGTCGCACTATCCACATCTGGG-3'(SEQ ID NO: 20); HO-1 forward 5'-CCTGGTGTCCCTTCAATCAT-3'(SEQ ID NO: 21), reverse 5'-GGCGATGAGGTGGAATACAT-3' (SEQ ID NO: 22); IDO-1 forward 5'-TGTGAACC-CAAAAGCATTTTTC-3'(SEQ ID NO: 23), reverse 5'-AAAGACGCTGCTTTGGCC-3'(SEQ ID NO: 24); TGF-β forward 5'-CCCAGCATCTGCAAAGCTC-3'(SEQ ID NO: 25), reverse 5'-GTCAATGTACAGCTGCCGCA-3' (SEQ ID NO: 26); Galectin-1 forward 5'-GGTCTGGTCGCCAGCAACCTGAAT-3'(SEQ ID NO: 27), reverse 5'-TGAGGCGGTTGGGGAACTTG-3'(SEQ ID NO: 28); IL-10 forward 5'-AAGCTGAGAACCAA-GACCCAGACATCAAGGCG-3'(SEQ ID NO: 29), reverse 5'-AGCTATCCCAGAGCCCCAGATCCGATTTGG-3' (SEQ ID NO: 30); and GAPDH forward 5'-AAGGTCG-GAGTCAACGGATTTGGT-3'(SEQ ID NO: 31), reverse 5'-AGTGATGGCATGGACTGTGGTCAT-3'(SEQ ID NO: 32).

Prostaglandin E2 Immunoassay

The measurement of prostaglandin E2 (PGE2) was repeated two times for all standards and samples. 100 μl of standard diluent (Tissue Culture Media) was placed in NSB and Bo (0 pg/ml standard material), and 100 μl of standard material was added to appropriate wells. Similarly, 100 μl of samples were added to the wells. Then, 50 μl of assay buffer was added to the NSB wells, and 50 μl of blue conjugate was added to each well except total activity (TA) and blank wells. Thereafter, μl of yellow antibody was added to each well, and incubated in a plate shaker (500 rpm or less) for 2 h. Each well was washed three times with 400 μl wash solution. After the last wash, a buffer for each well was removed, and the remaining washing buffer was removed using a lint free paper towel, and then, 5 μl of blue conjugate was added to the TA well. Then, 200 μl of pNpp substrate solution was added to each well. After the reaction was allowed to proceed at room temperature without vibration for 45 minutes, 50 μl of stop solution was added to each well, and then the absorbance was measured at 405 nm.

T Cell Proliferation Assay

Carboxyfluorescein diacetate succinimidyl ester (CFSE)-MLR assay was performed to determine the proliferation of CD4$^+$ and CD8$^+$ T cells co-cultured with MSCa and SOD3-transfected MSCs. The assay was performed by plating $1\times10^6$ CFSE-labeled responder cells (whole spleen cells from CS7BL/6 mice) in triplicate in 24-well plates (Costar, Corning, N.Y.). The cells were stimulated with $1\times10$ stimulator cells (Balb/c mouse cells) irradiated with 3000cGY. For CFSE labeling, $200\times10^6$ cells/ml of responder cells were resuspended in PBS. CFSE (Molecular Probes, Inc) was added to make a final concentration of 5 μM, and the cells, while protected from light, were gently shaken at room temperature for 10 minutes. CFSE labeling of cells was stopped by the addition of cold RPMI 1640 growth medium (GIBCO) and kept on ice for 5 minutes. The cells were pelleted and washed twice with the growth medium and resuspended. Both the CFSE-labeled responder cells and irradiated stimulator cells were adjusted to a concentration of $2\times10^6$ cells/ml in the growth medium, and co-cultured in a total volume of ml in 24-well plates with MSCs or SOD3-transfected MSCs at a ratio of 10:1 and incubated at 37 ☐, in 5% $CO_2$ and 100% humidity. After a 5-day culture period, cells were harvested, washed twice, and resuspended in PBS. Subordinate factors of responder cells were quantified by using the FITC conjugated anti-mouse CD4 and PE-conjugated anti-mouse CD8 (BD Biosciences Pharmingen).

T Cell Differentiation Assay

Naive CD4$^+$ T cells were isolated by negative selection from spleens and lymph nodes of C57BL/6 mice using MACS column (Miltenyi Biotech). The isolated cells were activated by plate-bound anti-CD3 antibody, and anti-CD28 antibody (2 μg/ml) added to RPMI 1640 medium containing 10% FBS, 2 mM glutamine, and 1% penicillin-streptomycin. The cells were polarized under Th1 polarizing conditions (10 μg/ml anti-IL4 Ab, 10 ng/ml IL-12), Th2 polarizing conditions (10 μg/ml anti-IFN-γ Ab, 10 ng/ml IL-4), Th17 polarizing condition (20 ng/ml IL-6, 5 ng/ml TGF-β, 10 μg/ml IFN-γ antibody, 10 μg/ml IL-4 antibody) or Treg polarizing conditions (5 ng/ml TGF-β and 10 ng/ml IL-2), and then co-cultured with MSCs or SOD3-transfected MSCs at a ratio of 10:1 for 4 days. All cytokines and antibodies used for CD4$^+$ T cell differentiation were purchased from BD Biosciences. After 4 days, the cells were harvested for mRNA expression analysis using cytokines or molecules specific for Th1, Th2, Th17, or Treg cell differentiation.

Experimental Models and Disease Models

The mice used in the experiments were 8-week aged C57BL/6 mice and fed with standard mouse feed and water without specific pathogen, and the experiments were performed following the regulations of the Catholic Ethics Committee of the Catholic University in accordance with the guidelines of the Ministry of Health and Welfare.

For induction of chronic and aggressive inflammation on skin of the mice, the hair of the back of the mice was removed by shaving, and 62.5 mg of imiquimod (IMQ) cream (5%, Aldara 3M pharmaceuticals) were applied to the skin of the shaved mice.

For introduction of atopy-like dermatitis, a mixture of 10 μg of OVA protein and 4 mg of aluminum hydroxide as an antigen adjuvant was intraperitoneally injected into mice grown in SPF conditions at the start of the experiment (D0), day 7 (D7), and day 14 (D14), so that the animals were sensitized. From day 21 after the start of the experiment, a patch was prepared by wetting 1×1 $cm^2$ gauze in 100 μg of OVA dissolved in 100 μl of PBS, and then attached to the shaved back of the mice to induce immune responses for 7 days. The immune responses were again induced by OVA patch in the same manner for one week starting from day 35. MSCs, LacZ-MSCs, and SOD3-MSCs were injected into the lesion site on day 42 after the start of the experiment, and skin changes were observed to the naked eye on day 49.

Subcutaneous Injection of MSCs into Mice

In the animal experiments using IMQ and ovalbumin, the subcutaneous injection of MSCs was conducted by subcutaneously injecting MSCs into mice at a cell number of $2\times10^6$ cells for each experimental condition. Equal volume of phosphate buffered saline (PBS), which is a control for MSC subcutaneous injection, was subcutaneously injected.

Analysis of cAMP Concentration in Mouse Skin

The back skin cells and blood plasma were obtained from the mice at day 6 and 12 after IMQ coating to determine the cAMP concentration. For cAMP concentration analysis, cAMP ELISA kit (BD immunocytometry) was used.

Histological Evaluation and Fluorescent Immunohistochemistry in Mouse Models

The back skin cells were obtained from mice at day and 12, and fixed in 4% paraformaldehyde (PFA) and embedded in paraffin. For skin samples, 4 μm-thick tissue sections were prepared using a rotary microtome (Leica). Then, the tissue sections were dewaxed using xylene and dehydrated through gradients of alcohol. The pre-treated tissue sections were then stained with Hematoxylene and eosin stain (H and E stain). The fluorescent immunohistochemistry was performed by incubated the tissue sections with primary antibodies against CD4, CD8, CD11c, or Gr-1 and then proper fluorescence-labeled secondary antibodies against Alexa fluor 488 and Alexa fluor 647.

Flow Cytometry Analysis of Mouse Splenocytes

Total spleen cells were harvested from each group of mice and resuspended in MACS buffer (1×PBS with 0.5% BSA). The cells were stained with FITC-conjugated anti-mouse CD4, PE-conjugated anti-mouse CD8, APC-conjugated anti-mouse Gr1, and PE-conjugated anti-mouse CD11c. After the staining was done for 30 minutes, the cells were washed with MACS buffer, followed by centrifugation, and then the cells were resuspended in 500 μl of MACS buffer for FACS analysis.

Reverse Transcriptase-PCR and Real-Time Quantitative PCR for Mouse Skin Gene Expression Analysis Total RNA was isolated from mouse back skin using TRIzol reagent (Invitrogen). cDNA was synthesized from 1 ug of total RNA using a reverse transcription system (Qiagen, Hilden, Germany). Primer sets of IL-1α (QT00113505), IL-1β (QT00021385), IL-4 (QT00160678), IL-6 (QT00182896), IL-10 (QT00106169), IL-17 (QT00103278), IL-20 (QT00126735), IL-22 (QT00128324), IL-23 (QT01663613), IFNγ (QT00000525), TNF-α (QT01079561), TGF-(QT00025718), CXCL-1 (QT00199752), CCL20 (QT00261898), and GAPDH (QT02448075) were purchased from Qiagen (The serial number in parentheses is the Qiagen catalog number). Primer sequences for determining the expression levels of Foxp3, T-bet, GATA3, RORγt, and SOD3 are as follows: Foxp3 forward GCAACAGCACTGGAACCTTC(SEQ ID NO: 5), Foxp3 reverse GCATTGCTTGAGGCTGCGTA (SEQ ID NO: 6); T-bet forward AGCCAGC-CAAACAGAGAAGA(SEQ ID NO: 7), T-bet reverse AATGTGCACCCTTCAAACCC(SEQ ID NO: 8); GATA3 forward ACATGTCATCCCTGAGCCAC(SEQ ID NO: 9), GATA3 reverse AGGAACTCTTCGCACACTTG(SEQ ID NO: 10); RORγt forward GCCTACAATGCCACCACC (SEQ ID NO: 11), RORγt reverse ATT GAT GAG AAC CAG GGC(SEQ ID NO: 12); SOD3 forward TGTTG-GAGCAGAGGAGAAGCTCAAC(SEQ ID NO: 13); and SOD3 reverse AAGCTCTCTTGGAGCAGCTGGAAA (SEQ ID NO: 14). GAPDH mRNA was used as an endogenous control. PCR was performed using Rotor-Gene 6000 (Corbett) and QuantiTect SYBR Green PCR Kit(Qiagen). The amplification program consisted of 1 cycle at 95 □ for 10□min, followed by 35 cycles of at 95□ for 20 □seconds, 55□ for 20□seconds, and 72□ for 20□ seconds.

Western Blot for Mouse Skin Protein Expression Analysis

Total protein was extracted using mice back skin. Equal amount of proteins were loaded per lane, followed by electrophoresis, and the proteins are blotted on membranes. Target proteins were incubated with primary antibodies specific for target molecules and detected using enhanced chemiluminescence system (GE health care Life Sciences).

Statistical Analysis

Data was expressed as means±SD, and statistical significance was assessed by student t-test or ANOVA for independent groups. Statistically significant differences are indicated by *, $, #in the drawings.

All the experiments were repeated three times unless otherwise stated.

Example 1

Production of Mesenchymal Stem Cells (MSCs) Overexpressing SOD3 and Verification of Efficacy Thereof <1-1> Confirmation of SOD3 Overexpression in SOD3-Transfected MSCs SOD3 protein expression patterns and SOD3 activity of human SOD3 gene-transfected mesenchymal stem cells (MSCs) were investigated.

MSCs were transfected with human SOD3 gene using electrophoresis and harvested after 24 hours, and the protein expression levels were investigated by performing RT-PCR and western blot. The SOD3 activity was determined by measuring the amount of superoxide radicals present in the cell culture solution cultured for 24 hours.

As shown in FIG. 1, it can be seen that SDO3 mRNA (FIG. 1A) and SOD3 protein (FIG. 1B) were overexpressed in SOD3-transfected MSCs (SOD3-MSC) compared with untransfected MSCs (MSC). In addition, with respect to SOD3 activity, SOD3-MSCs showed remarkably higher SOD3 activity than MSCs (FIG. 1C). It was verified that SOD3-transfected MSCs overexpressed SOD3 and had high SOD3 activity.

<1-2> Reduction of Reactive Oxygen Species in SOD3-Transfected MSCs

The amount of reactive oxygen species (ROS) generated due to TNF-α/IFN-γ stimulations in SOD3-transfected MSCs was investigated.

MSCs were transfected with human SOD3 gene using electrophoresis, and stimulated with TNF-α (10 ng/ml) and IFN-γ (100 U/ml) for 1 hour. The generated ROS were fluorescence-stained with H2DCF-DA and measured using a fluorescence spectrophotometer.

Figure 2:
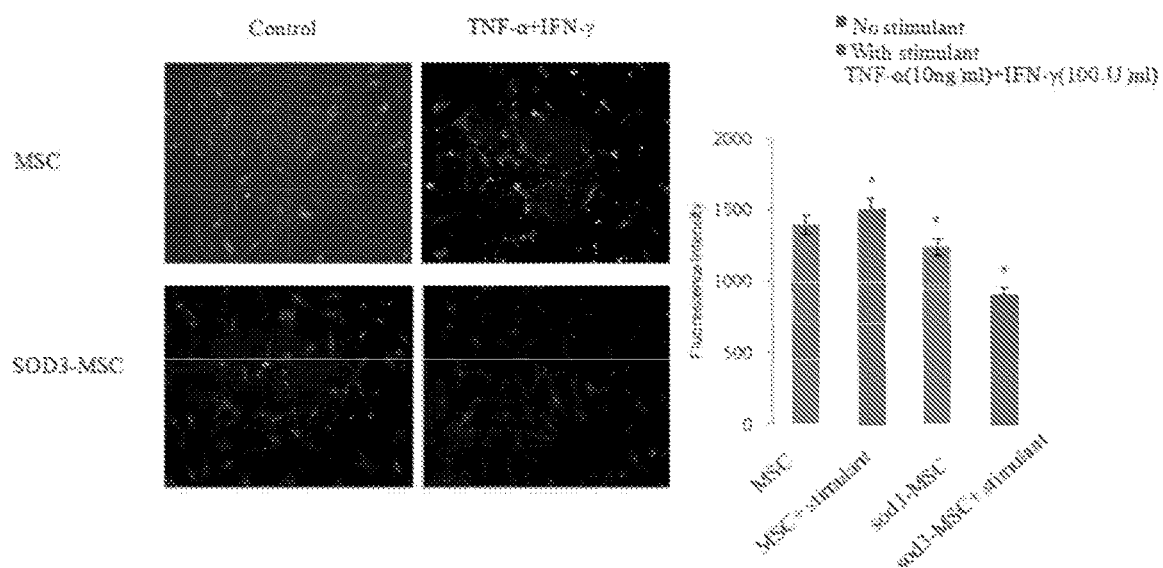
FIG. 2 shows fluorescent staining images and a fluorescence spectrophotometry result graph to observe reactive oxygen species generated by TNF-α and IFN-γ stimulation in SOD3-MSCs and MSCs.

As shown in FIG. 2, ROS were generated in large amounts due to TNF-α/IFN-γ stimulations to show strong fluorescence intensity in untransfected MSCs, but the amount of ROS was not greatly changed even after the stimulations with TNF-α/IFN-γ in SOD3-MSCs compared with a control treated with PBS, and a fluorescence reduction tendency was rather observed. That is, it was verified that the reactive oxygen species generation ability was greatly suppressed in SOD3-MSCs compared with untransfected MSCs.

<1-3> Effect of SOD3 Transfection on Cell Proliferation of MSCs

The effect of SOD3 transfection on the proliferation of MSCs was investigated using MTT assay.

Figure 3:
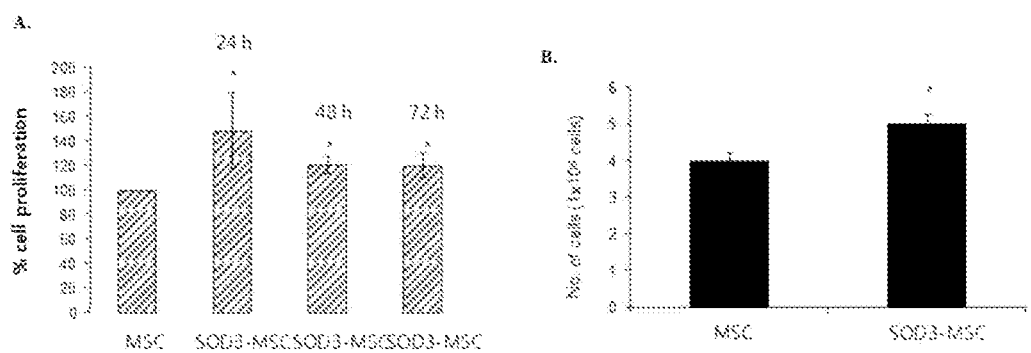
FIG. 3 shows MTT assay results over time (FIG. 3A) and the number of measured cells (FIG. 3B) to investigate effects of SOD3 transfection on MCS proliferation.

As shown in FIG. 3, compared with the untransfected MSCs, SOD3-MSCs showed an improvement in cell proliferation (FIG. 3A) and a remarkable increase in the number of cells (FIG. 3B) up to 72 hours from 24 hours after the transfection. The above results indicate that SOD3-induced transfection promotes the cell proliferation of MSCs. The increased cell proliferation activity of SODS-transfected MSCs suggests the possibility that SOD3-transfected MSCs have higher therapeutic efficiency when developed into cell therapeutic agents for inflammatory diseases.

<1-4> Inhibitory Effect of SODS-Transfected MSCs on Expression of Inflammation-Related Cytokines The effect of SOD3-transfected MSCs on the expression levels of cytokines, which are important mediators in inflammatory responses, was investigated.

SOD3-MSCs resulted from the transfection by electrophoresis or MSCs were stimulated with TNF-α and IFN-γ for 12 hours while co-cultured with the human keratinocytes HaCaT cells, and then HaCaT cells were harvested. The levels of various inflammatory cytokines expressed by HaCaT cells are measured by qRT-PCT.

Figure 4:
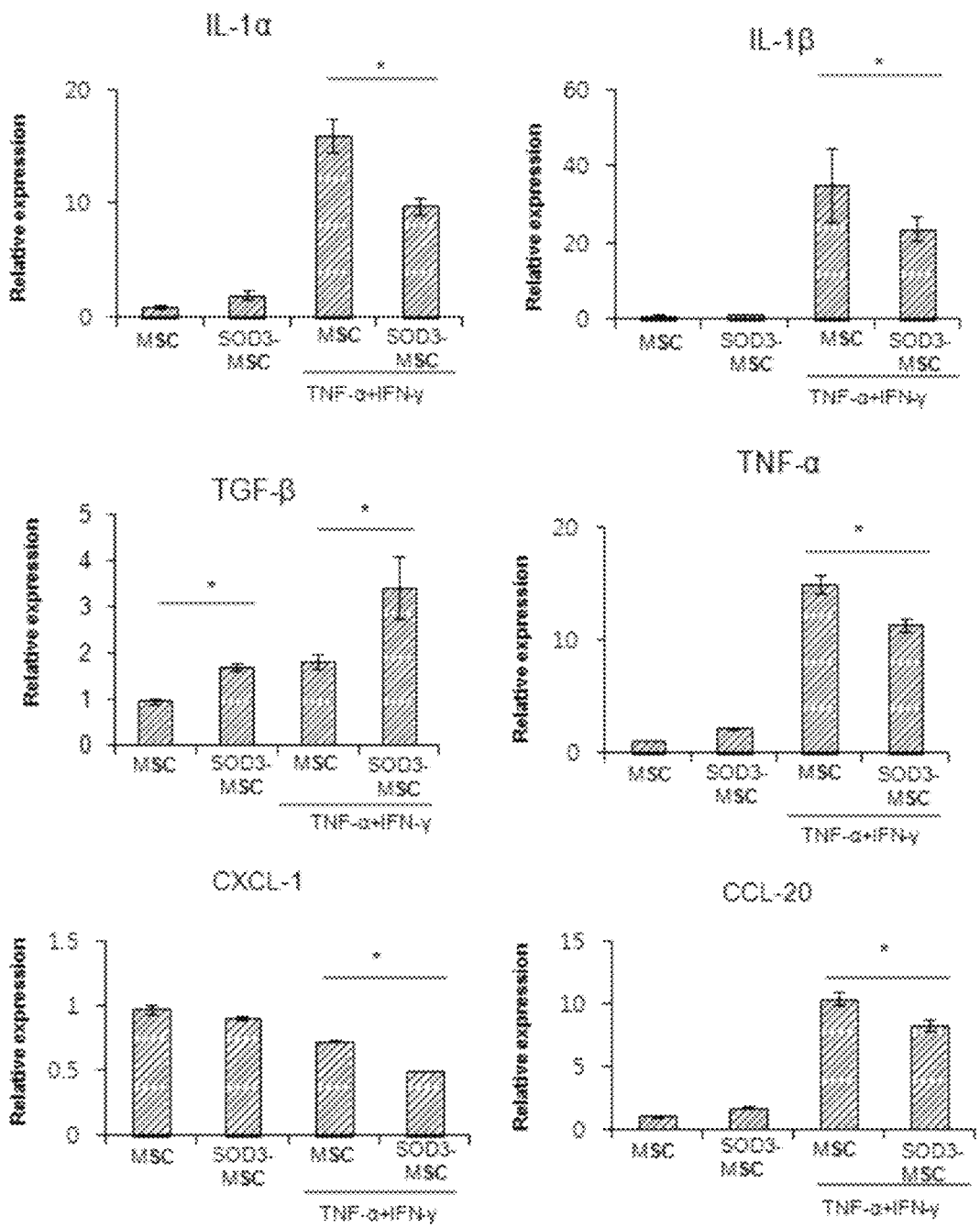
FIG. 4 shows RT-PCR results to investigate effects of SOD3-MSCs or MSCs on the expressions of inflammation-related cytokines of HaCaT cells.
Figure 5:
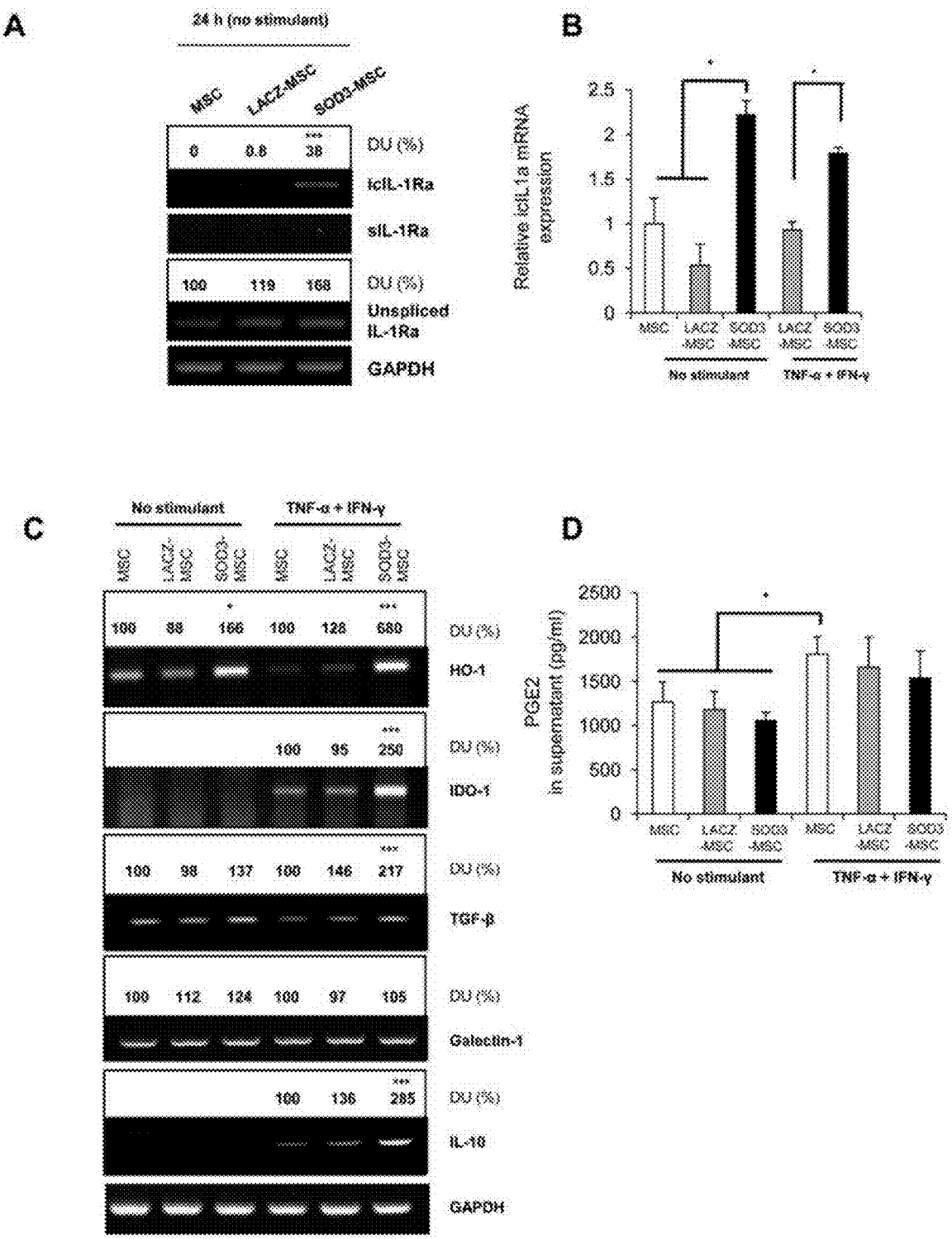
FIG. 5 shows expression levels of intracellular IL-1Ra (icIL-1Ra), soluble IL-1Ra(sIL-1Ra), and unspliced IL-1Ra measured by RT-PCR (FIG. 5A), quantitative analysis of icIL-1Ra mRNA level (FIG. 5B), expression levels of HO-1, DIO-1, TGF-β, Galectin-1, and IL-10 (FIG. 5C), and PGE2 level in culture media of corresponding cells measured by immunoassay (FIG. 5D) in MSCs, LacZ-transfected MSCs (LACZ-MSC), and SOD3-transfected MSCs (SOD3-MSC).
Figure 6:
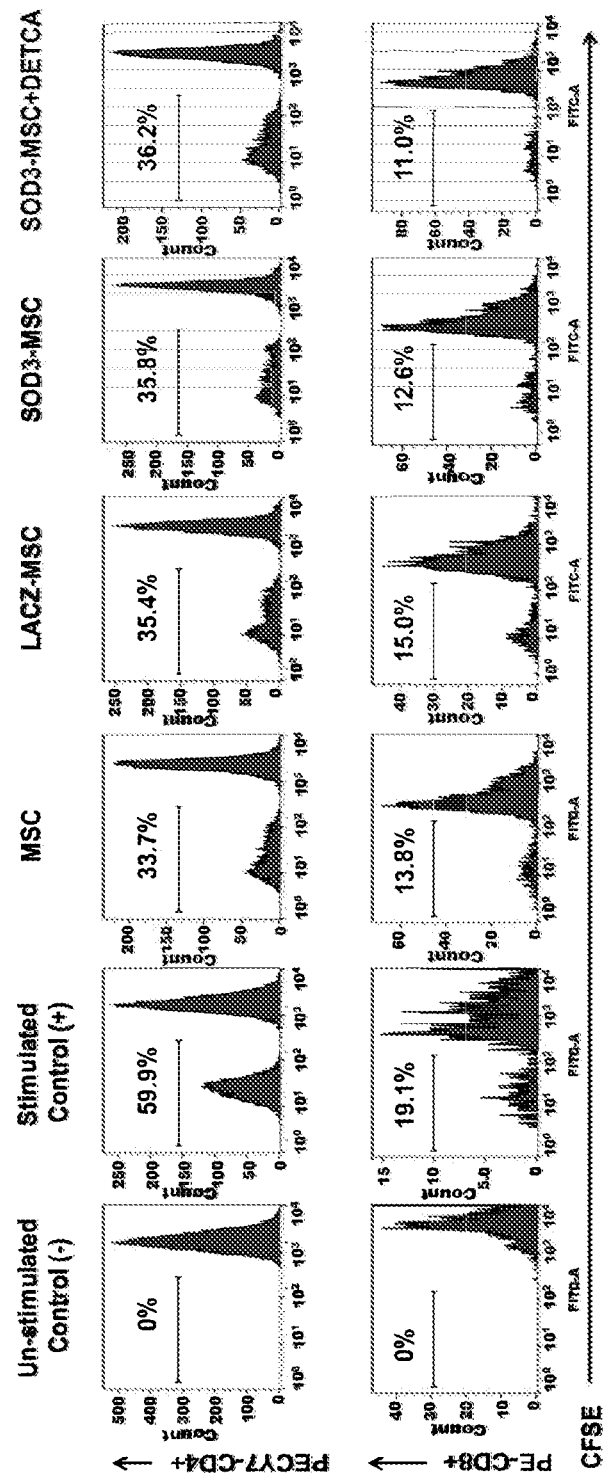
FIG. 6 shows flow cemetery (FACS) results to determine CD4⁺ T and CD8⁺ T cell proliferation in CFSE based-mixed lymphocyte reaction experiments co-cultured with a negative control (Control (−)), a positive control (Control (+), and, according to experimental conditions, untreated MSCs (MSC), LacZ-transfected MSCs (LACZ-MSC), SOD3-transfected MSCs (SOD3-MSC), and SOD3-trandsuced MSCs treated with DETCA (SOD3-MSC+DETCA). DETCA is an SOD3 inhibitor.

As shown in FIG. 4, the mRNA expression levels of IL-1α, TNF-α, and CCL-20 cytokines were greatly increased by TNF-α and IFN-γ stimulations in HaCaT cells co-cultured with MSCs (MSC) and the expression levels of the above cytokines were effectively suppressed in HaCaT cells co-cultured with SOD3-transfected MSCs overexpressing SODS (SODS-MSCs). As for CXCL-1, the expression level was hardly changed due to TNF-α and IFN-γ stimulations in HaCaT cells co-cultured with untransfected MSCs (MSC), but the expression level was further reduced in HaCaT cells co-cultured with SOD3-MSCs (SOD-MSC). As for TGF-which is both an anti-inflammatory cytokine and a Treg marker, HaCaT cells co-cultured with SOD3-MSCs (SOD-MSC) showed a higher expression level than HaCaT cells co-cultured with untransfected MSCs (MSC) in the absence of TNF-α and IFN-γ stimulations, and the increase width was observed to be further enlarged due to TNF-α and IFN-γ treatments.

The above results indicate that MSCs overexpressing and secreting SOD3, compared with MSCs not-overexpressing SOD3, inhibited the expressions of inflammatory cytokines induced by TNF-α and IFN-γ more effectively and improved the expressions of anti-inflammatory cytokines greatly in co-cultured neighboring HaCaT cells, thereby regulating inflammatory responses multi-directionally and effectively.

<1-5> Analysis of Immunosuppression-Related Molecule Expressions in SOD3-Transfected MSCs The expression patterns of immunosuppression-related materials expressed in SOD3-transduced MSCs were analyzed.

MSCs were incubated and transfected with AdLacZ or AdSOD3 adenovirus, and the intracellular mRNA expression levels of intracellular IL-1Ra (icIL-1Ra), soluble IL-1Ra (sIL-1Ra), unspliced IL-1Ra, HO-1, IDO-1, TGF-β, aalectin-1, and IL-10 were measured using RT-PCR in the presence or absence of TNF-α (10 ng/ml) and IFN-γ (100 U/ml) (A to FIGS. 5A and 5C). The relative expression level of icIL-1Ra was analyzed by real-time PCR (FIG. 5B), and GAPDHA was used as a control. In addition, supernatants in which MSCs were cultured were obtained, and the PGE2 concentration was determined using PGE2 ELISA kit (Enzo Life Sciences, NY, USA).

As shown in FIG. 5A to 5C, the expression levels of various genes having immunosuppressive functions, such as icIL-1Ra, TGF-β, IL-10, HO-1, and IDO-1, were significantly increased in MSCs transfected to overexpress SOD3 (SOD3-MSC) compared with untransfected MSCs (MSC) or LacZ-transfected MSCs (LacZ-MSC) as a control. Interestingly, the expressions of IDO-1 and IL-10 were increased in MSCs stimulated with TNF-α and IFN-γ, but the expressions of these genes were further increased in SOD3-MSCs. However, it was observed that the overexpression of SOD3 did not greatly affect the amount of PGE2 secreted (FIG. 5D) or the expression level of galactin-1.

It has been reported that the number of graft-infiltrating leukocytes was sharply reduced in transplant patients administered with IL-1Ra (Shiraishi M et al., *J Surg Res.*, 58(5): 465-470, 1995). It can be therefore expected that the expression of IL-1Ra is greatly increased in MSCs overexpressing SOD3, through which the inflammation responses and transplant rejection can be effectively suppressed in transplant patients.

Meanwhile, TGF-β and HO-1 are involved to promote the production of IL-10 and the formation of immunosuppressive Treg cells but inhibit pro-inflammatory cytokines in vitro and in vivo. HO-1 was confirmed to inhibit Th17 responses and exhibit anti-inflammatory activity by inhibiting p-STAT3-RORγt pathway to regulate the kinetics of RORγt and Foxp3 expressions, so that HO-1 is a novel therapeutic target for asthma, psoriasis, atopic dermatitis, and the like. In addition, human MSCs has been known to be able to induce the expression of indoleamine-2,3-dioxygenase-1 (IDO-1), and IDO-1 has been received as a key regulator of autoimmune diseases, such as acute graft-versus-host disease (GVHD), by inhibiting T cell proliferation and inducing apoptosis of immune cells to induce immunosuppression. Therefore, as verified in the above examples, the induction of activation of the catabolic pathway of tryptophan, such as HO-1 or IDO-1 by the overexpression of SOD3 in MSCs can be a potent therapeutic target for a number of autoimmune diseases.

<1-6> Effect of SOD3-Transfected MSCs on T Cell Proliferation

The effect of SOD3-transfected MSCs on the inhibition of T cell differentiation and proliferation was investigated.

Figure 7:
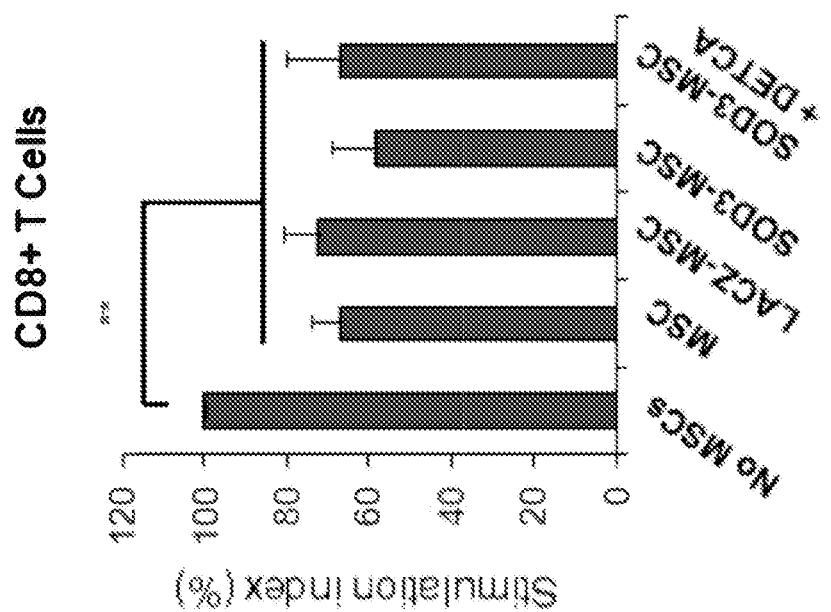
FIG. 7 shows graphs quantifying the FACS results of FIG. 6. "Stimulation index (1)" on the vertical axis indicates the number of cells when stimulation was applied/the percentage of cells when stimulation was not applied.
Figure 7:
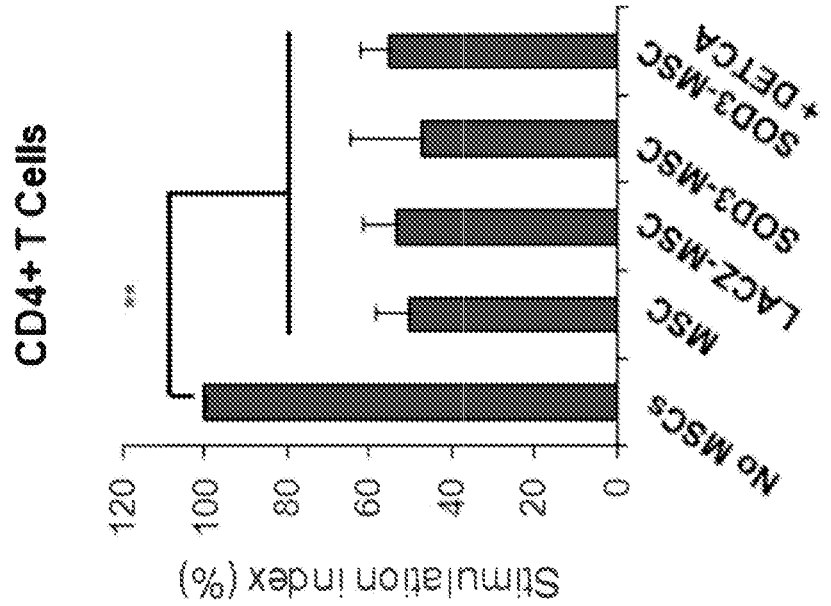

The CFSE based-mixed lymphocyte reaction (MLR) experiment was performed while T cells isolated from different species of mice (C67BL/6 and BalB/C) were co-cultured without MSCs, or with untreated MSCs, LacZ-transfected MSCs, or SOD3-transfected MSCs according to the experiment condition, and then flow cytometry was subjected to $CD4^+$ or $CD8^+$ cells (FIG. 6) and the flow cytometry assay results were quantified (FIG. 7). As shown in FIG. 7, the proliferation of $CD4^+$ T cells and $CD8^+$ T cells was suppressed in the co-culture with untreated MSCs (MSC) or LacZ-transfected MSCs (LACZ-MSC) compared with the co-culture without MSCs (No MSCs), and the proliferation of T cells was further suppressed in the co-culture with SOD3-transfected MSCs (SOD3-MSC). Meanwhile, SOD3-MSCs treated with the SOD3 inhibitor DETCA (SOD3-MSC+DETCA) showed a T cell proliferation inhibitory effect at similar levels to untreated MSCs (MSC). That is, it can be seen that the T cell proliferation inhibitory effect of SOD3-transfected MSCs is further enhanced due to the activity of overexpressed SOD3 than that of untransfected MSCs.

<1-7> Effect of SOD3-Transfected MSCs on T Cell Differentiation

The effect of SOD3-transfected MSCs on T cell differentiation was investigated.

Naïve T cells were co-cultured with untreated MSCs (MSC), LacZ-MSCs, or SOD3-MSCs according to the experimental conditions in each differentiation condition of Th1, Th2, Th17, or Treg cells, and the expression levels of differentiation-related major transcription factors expressed by differentiated T cells were measured by real-time qRT-PCR.

Figure 8:
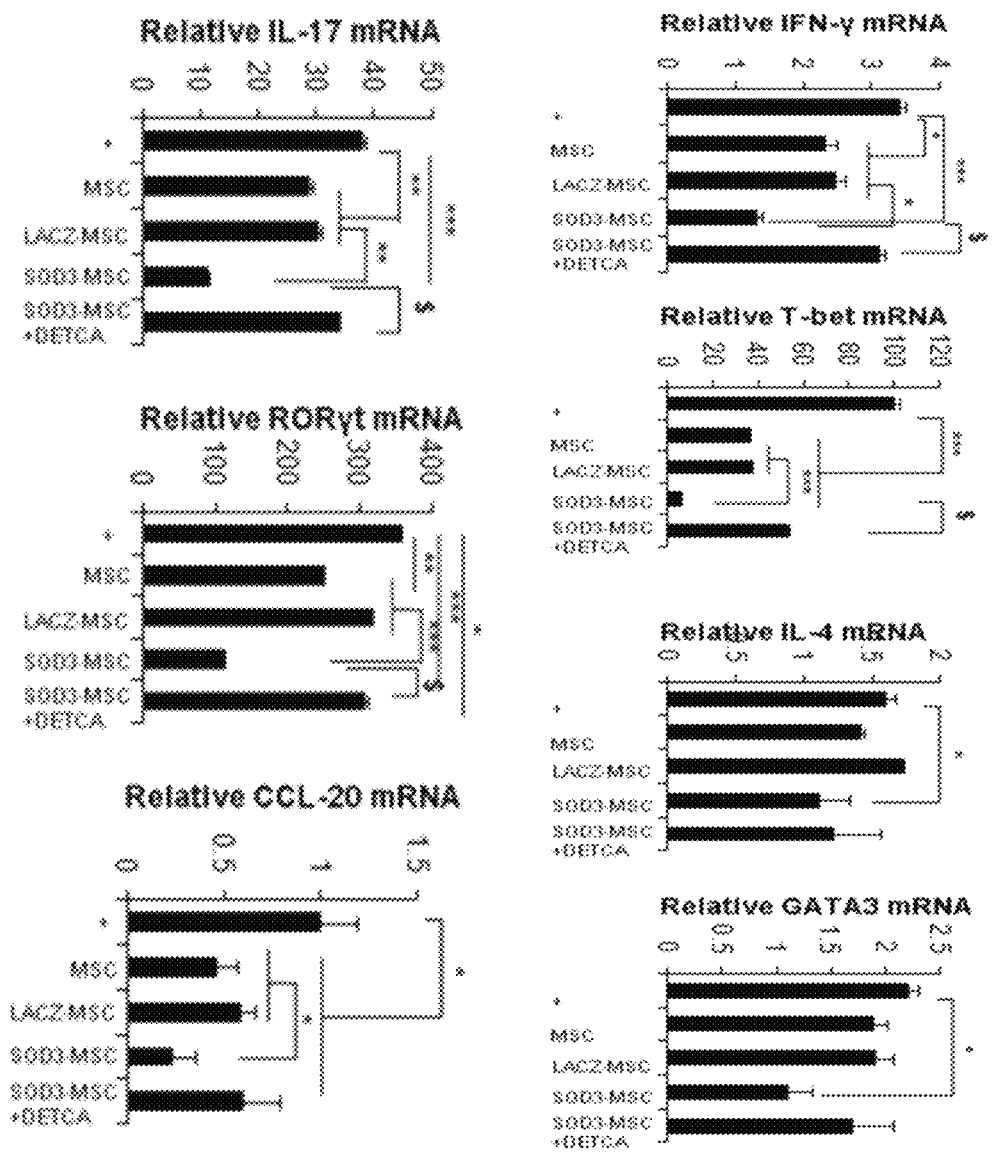
FIG. 8 shows graphs depicting RT-PCR results to determine the expression levels of T-cell lineage-specific master transcription factors and cytokines.

As shown in FIG. 8, the expression patterns of lineage-specific transcription factors and cytokines IFNγ, T-bet, IL-4, GATA3, IL-17, RORγt, and CCL20 of T cells cultured in Th1, Th2, and Th17 differentiation conditions were determined by mRNA measurement, and as a result, it was verified that the expressions of the above genes were reduced in T cells co-cultured with untreated MSCs (MSC) or LacZ-MSCs (LACZ-MSC) compared with a control co-cultured without MSCs ((+) in FIG. 7), and the expressions of the transcription factors and cytokines were further remarkably reduced in the cells co-cultured with SOD3-MSCs. The gene expression inhibitory effect by SOD3-MSCs was more potent for Th17 cell-specific genes IL-17, RORγt, and CCL-20. Meanwhile, the co-culture with SOD3-MSCs added with the SOD3 inhibitor DETCA (SOD3-MSC+DETCA) showed the gene expression inhibitory effects at similar levels to the co-culture with MSCs or LacZ-MSCs, and these results indicate that the synergistic effect of SOD3-MSCs on the inhibition of gene expression is induced by SOD3 activity.

Figure 9:
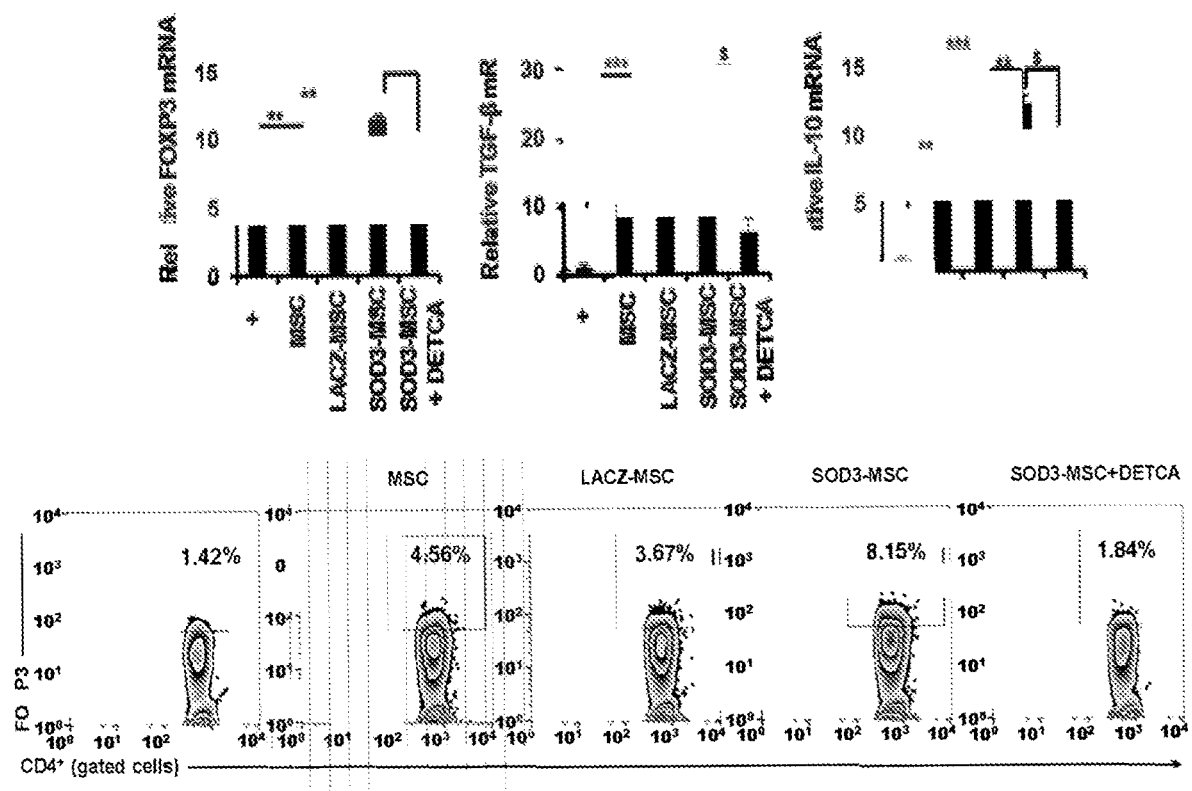
FIG. 9 shows RT-PCR results (upper) to determine the expression levels of Treg lineage-specific master transcription factors and cytokines and flow cemetery results (lower) depicting effects of MSCs on Treg cell differentiation.
Figure 10:
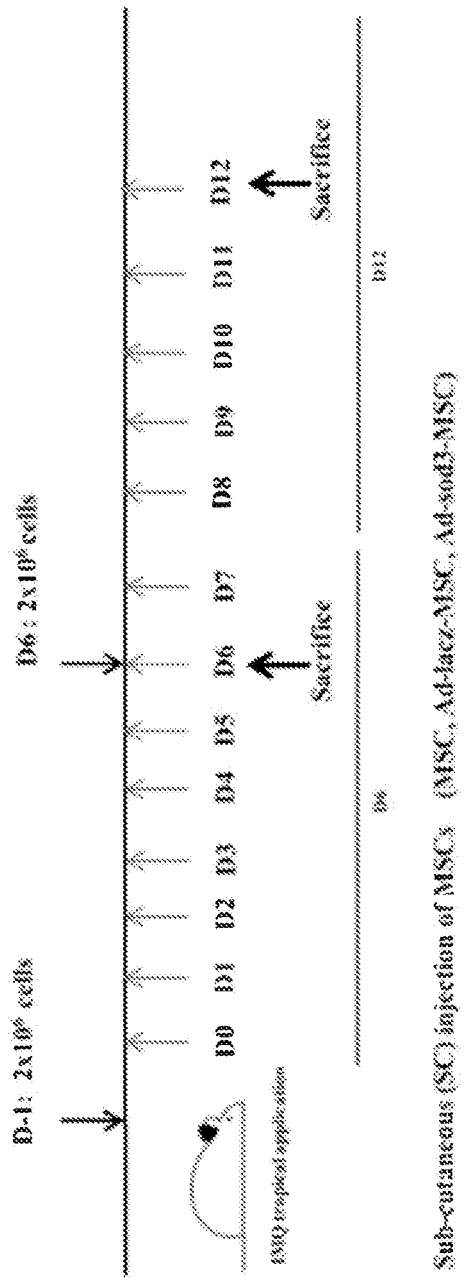
FIG. 10 is a schematic diagram showing an experimental setup for mice with IMQ-induced chronic and aggressive dermatitis.

As shown in FIG. 9, the expression patterns of lineage-specific transcription factors and cytokines Foxp3, TGF-β, and IL-10 of T cells cultured in Treg differentiation conditions were determined by mRNA measurement, and as a result, it was verified that the expressions of the above genes were increased in T cells co-cultured with untreated MSCs (MSC) or LacZ-MSC(LACZ-MSC) compared with a control co-cultured without MSCs (+) in FIG. 9), and the expressions of the transcription factors and cytokines were further remarkably increased in the cells co-cultured with SOD3-MSCs. Especially, the increase effect of SOD3-MSCs on FOXP3 expression could be verified at the cellular level by flow cytometry (lower part in FIG. 9). Meanwhile, the co-culture with SOD3-MSCs added with the SOD3 inhibitor DETCA (SOD3-MSC+DETCA) showed the gene expression inhibitory effects at similar levels to the co-culture with MSCs or LacZ-MSCs, and these results indicate that the synergistic effect of SOD3-MSCs on the increase of Treg-related gene expression is induced by SOD3 activity.

These results indicate that SON transfection remarkably increases the original T cell differentiation regulatory effect of MSCs, and especially suggest the possibility that SOD3 transfection can suppress inflammation more effectively by lowering the differentiation of Th17 cells acting as pathogenic cells and inducing the differentiation of Treg cells having an inflammation-modulating effect in inflammatory diseases.

Example 2

Imiquimod-Induced Chronic and Aggressive Dermatitis Biological Models

<2-1> Skin Inflammation Inhibitory Effect of SOD3-Transfected MSCs

It was investigated whether SOD3-transfected MSCs has an inflammation-modulating effect in the body, on the basis of the regulatory effect of MSCs overexpressing SOD3 on T cell proliferation and differentiation, observed in <Example 1>.

The imiquimod (IMQ), which is known to induce psoriasis-like acute and aggressive dermatitis by activating signaling of the innate immune system, was applied to the shaved back skin in mice every day to induce skin inflammation responses. According to the experimental setup in FIG. 10, each group of mice (five mice per group) were subcutaneously injected with untreated MSCs, LacZ-transfected MSCs, SOD3-transfected MSCs at $2 \times 10^6$ cells before IMQ application, and then IMQ was consecutively applied to the shaved back of the mice for 12 days, to conduct comparative observation of inflammation responses occurring the skin. For quantitative analysis of skin inflammation symptoms, the back skin tissue of the mice was collected, the tissue samples were stained with H&E, and the epidermal thickness was measured.

Figure 11:
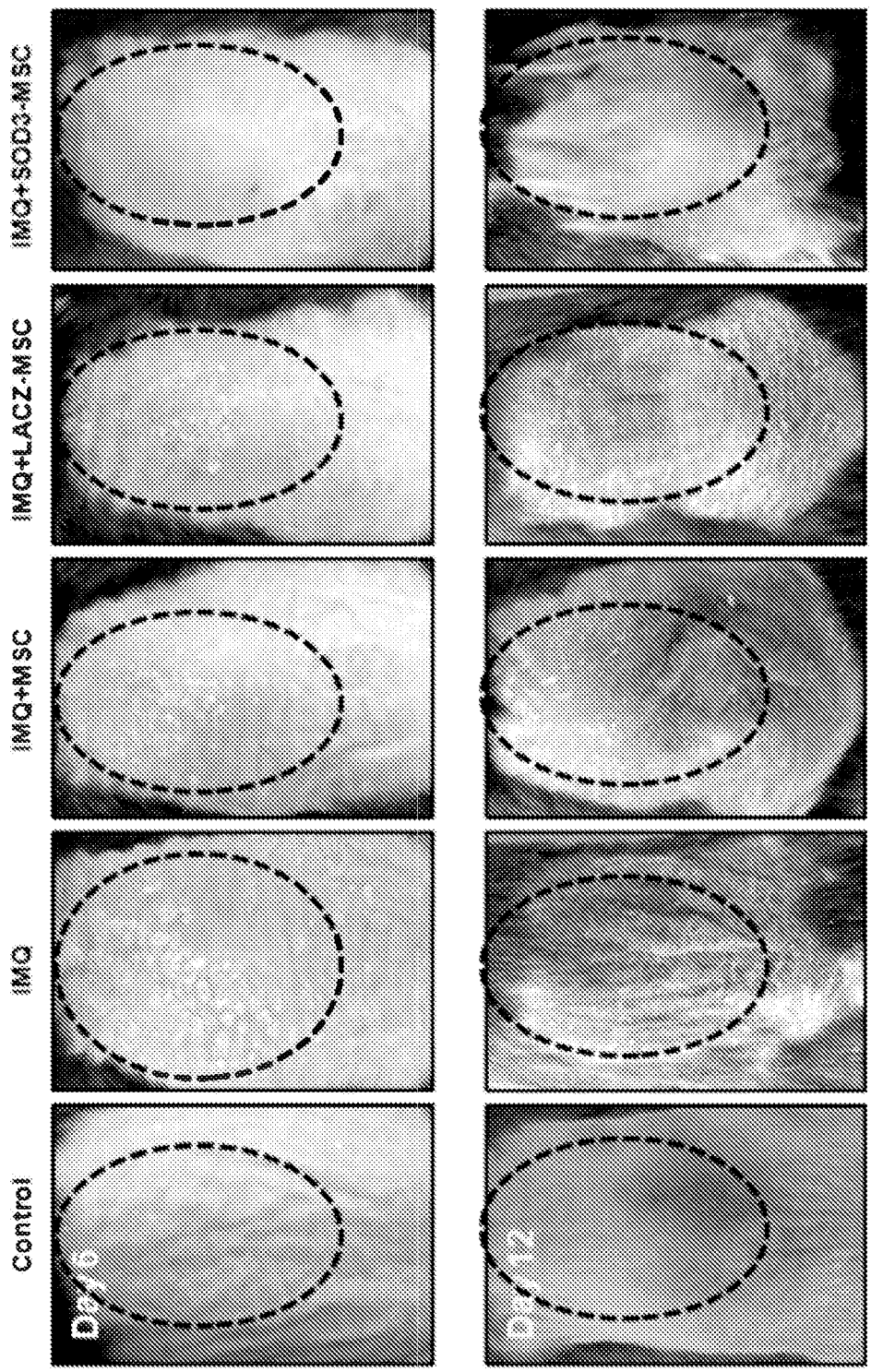
FIG. 11 shows images of mouse back skin depicting the lesion progression of each group of mice in the IMQ-induced chronic and aggressive dermatitis biological model experiments.

As shown in FIG. 11, compared with a control without IMQ application, the mice with the IMQ application without subcutaneous injection of MSCs started to display signs of erythema, scaling, and thickening, which can be confirmed by the naked eye, accompanied by inflammation symptoms, after 2-3 days. Such symptoms were clearly observed 6 days after the start of the experiment (Day 6), and continued until 12 days after the start of the experiment (Day 12). The mice injected with untreated MSCs (MSC) or LacZ-transfected MSCs (LACZ-MSC) showed a tendency to alleviate IMQ-induced skin symptoms. Meanwhile, the symptoms, such as erythema and scaling, were observed to be apparently reduced to the naked eye in the mice injected with SOD3-transfected MSCs (SOD3-MSC) compared with the mice injected with MSCs or LACZ-MSCs.

Figure 12:
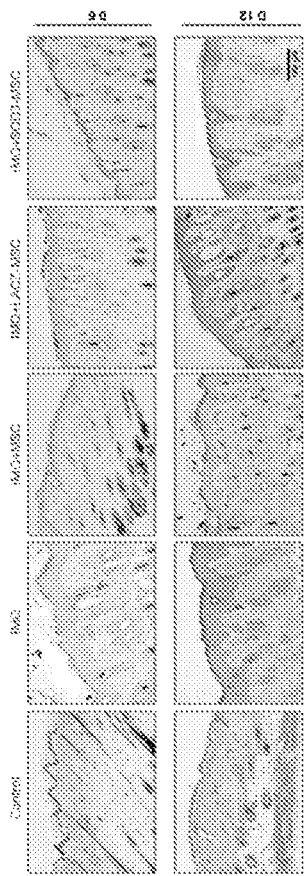
FIG. 12 shows microscopy images of back skin sections of each group of mice stained with H&E in IMQ-induced chronic and aggressive dermatitis mouse experiments.
Figure 13:
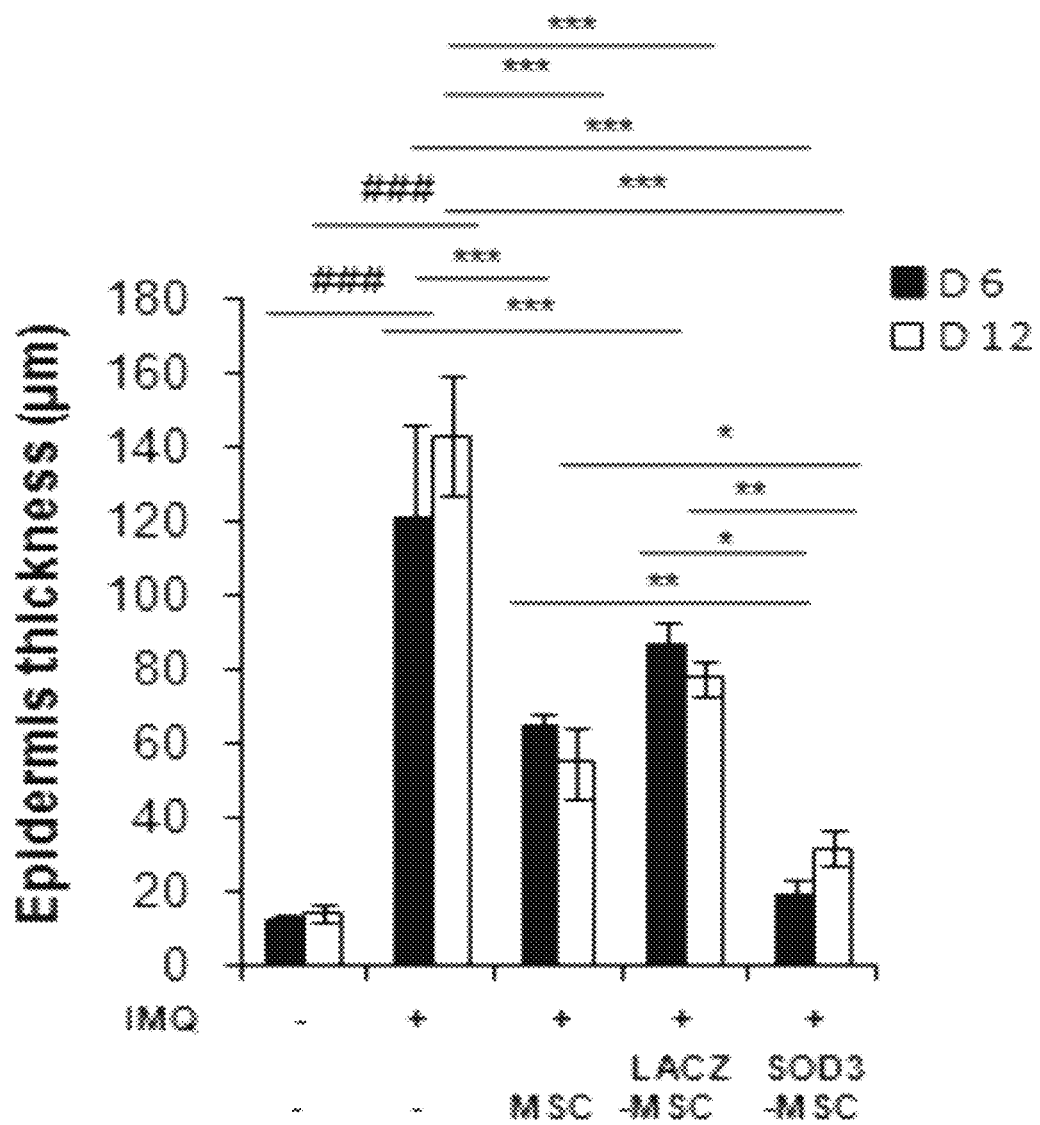
FIG. 13 shows a bar graph comparing epidermal thickness measurement results of back skin for each group of mice in IMQ-induced chronic and aggressive dermatitis mouse experiments.

As shown in FIGS. 12 and 13, the dermal thickness, which was measured from the skin tissue sections of control mice and each group of mice, also showed similar results compared with the skin inflammation conditions observed to the naked eye. IMQ application without MSC injection remarkably increased the epidermal thickness compared with the control, and the injection of MSCs or LacZ-MSCs reduced the IMQ-induced dermal thickness. Meanwhile, the mice injected with SOD3-MSCs showed little increase in the dermal thickness after IMQ application, which corresponded similar levels compared with the control without IMQ application. The epidermal thickness was significantly thin in the mice injected with SOD3-MSCs compared with the mice injected with MSCs or LacZ-MSCs.

These results indicate that MSCs, which overexpress SOD3 by SOD3 transfection, had a significant effect in the alleviation of skin inflammation compared with general MSCs.

<2-2> Inhibitory Effect of SOD3-Transfected MSCs on Infiltration of Neutrophils and Dendritic Cells The composition and recruitment of immune cells in spleens and skin of mice with IMQ-induced dermatitis were investigated.

Figure 14:
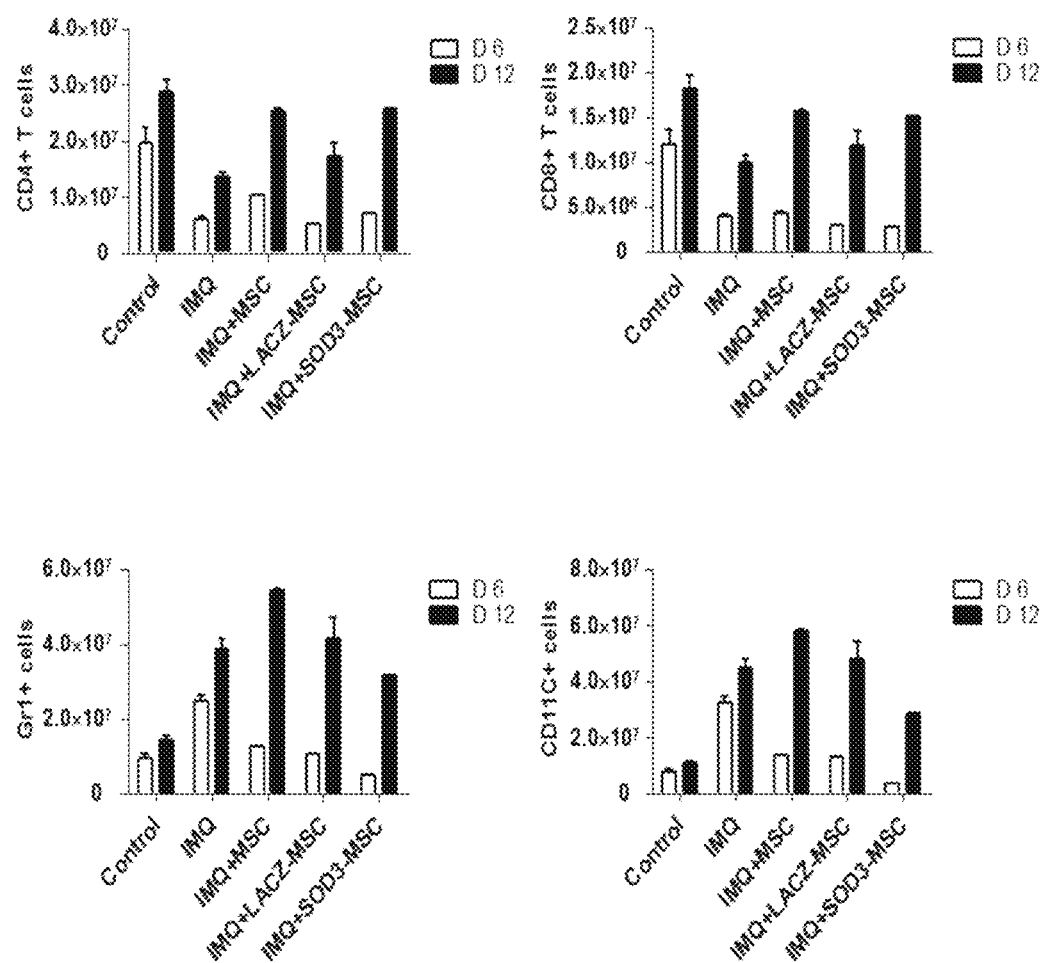
FIG. 14 shows graphs depicting the proportions of T cells, neutrophils (Gr1+), and dendritic cells (CD11C+) infiltrating into spleens of each group of mice in IMQ-induced chronic and aggressive dermatitis mouse experiments.
Figure 15:
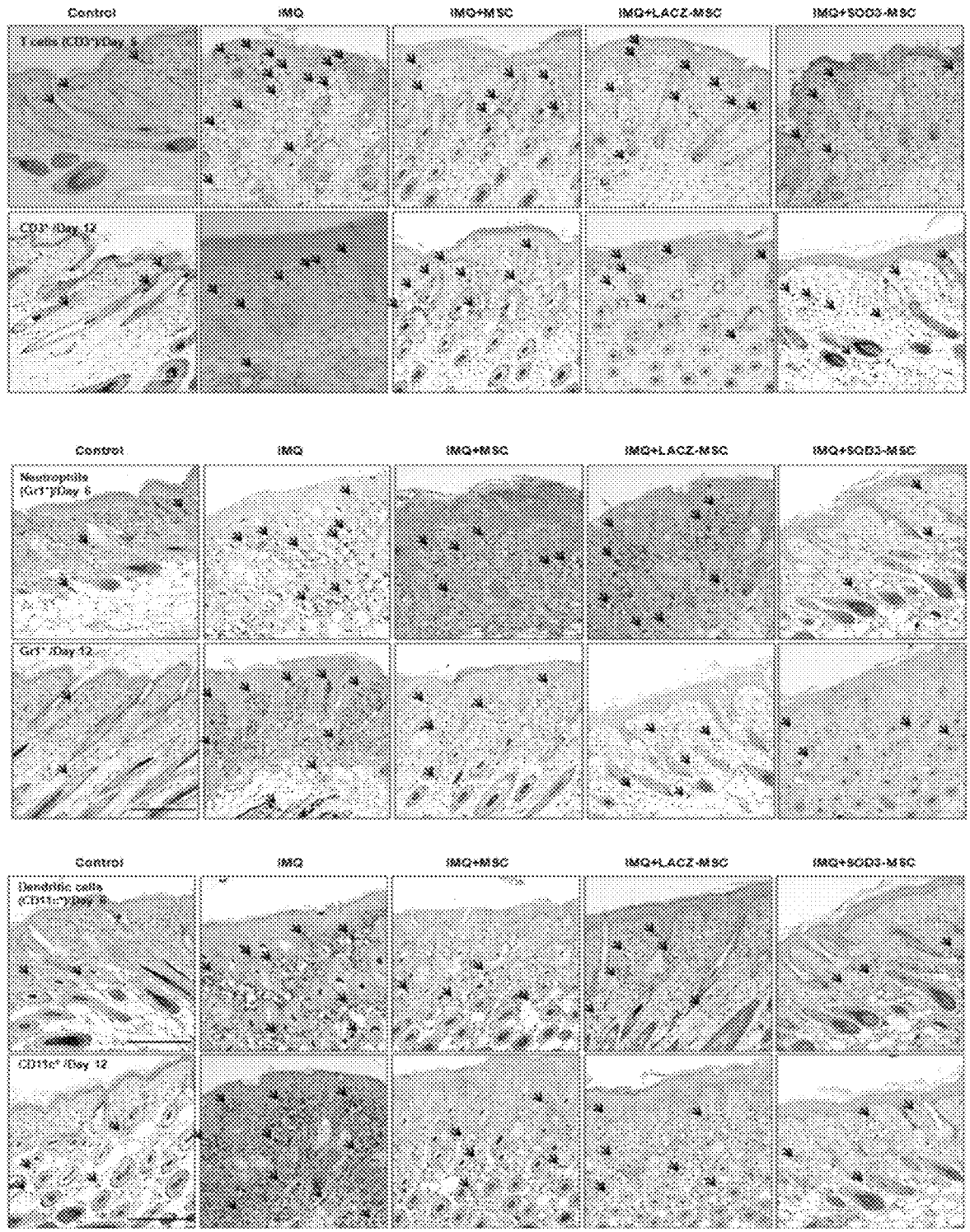
FIG. 15 shows microscopy images of T cells, neutrophils (Gr1+), and dendritic cells (CD11C+), which infiltrated into skin of each group of mice, stained and analyzed by immunohistochemistry, in IMQ-induced chronic and aggressive dermatitis mouse experiments. Arrows indicate stained cells.
Figure 16:
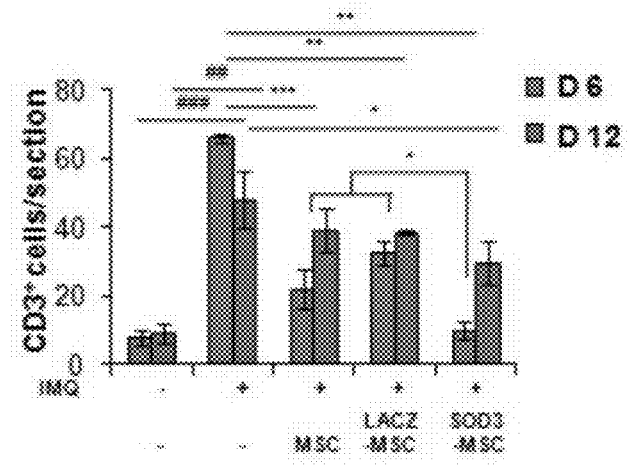
FIG. 16 shows graphs depicting the numbers of T cells, neutrophils (Gr1+), and dendritic cells (CD11C+) infiltrating into spleens of each group of mice in IMQ-induced chronic and aggressive dermatitis biological model experiments.
Figure 16:
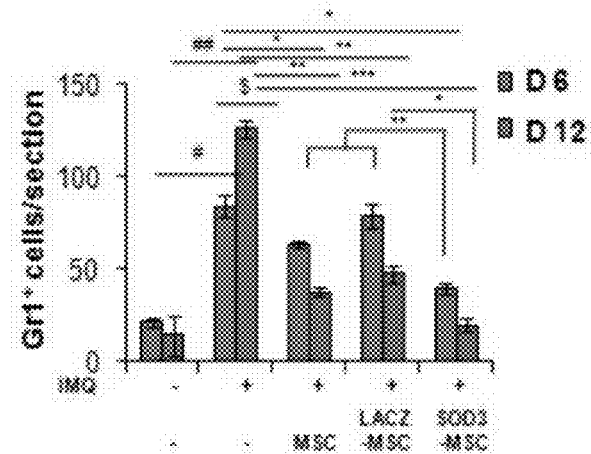
Figure 16:
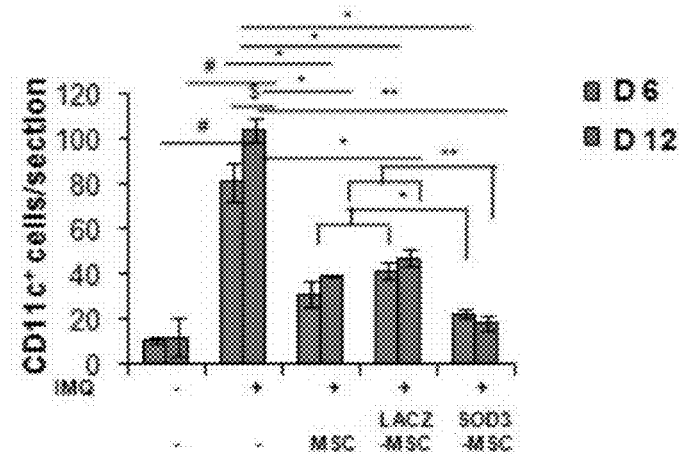

$CD4^+$ T cells, $CD8^+$ T cells, neutrophils ($Gr1^+$ cells), and dendritic cells ($CD11c^+$ cells), which constitute the spleens of the mice injected with respective types of MSCs according to the experimental conditions, were examined by flow cytometry (FIG. 14), and the back skin tissue sections of the mice with IMQ application were stained with different kinds of immune cell markers and the number of cells was measured (FIGS. 15 and 16).

As shown in FIG. 14, $CD4^+$ T cells and $CD8^+$ T cells were reduced in the spleens of the mice treated with IMQ compared with the control mice not treated with IMQ, and $CD4^+$ T cells and $CD8^+$ T cells were slightly increased in the mice injected with MSCs. On the contrary, the numbers of neutrophils ($Gr1^+$ cells) and dendritic cells ($CD11c^+$ cells) in the spleens were increased due to IMQ treatment, and the number of neutrophils and dendritic cells were reduced due to SODS-MSC treatment.

As shown in FIGS. 15 and 16, $CD3^+$ T cells, $CD8^+$ T cells (data not shown), neutrophils ($Gr1^+$), and dendritic cells ($CD11c^+$) were all remarkably increased in the skin due to IMQ treatment, and the infiltration of immune cells induced by IMQ was reduced in the mice treated with MSCs or LacZ-MSCs. The filtration was further suppressed in the mice treated with SOD3-MSCs than the mice treated with the other types of MCSs, and thus T cells, neutrophils, and dendritic cells in the skin tissues were observed to be all remarkably reduced.

<2-3> Inhibitory Effect of SOD3-Transfected MSCs on Expression of Inflammation Response Mediators The expression patterns of cytokines in the back skin of the mice with skin inflammations induced by IMQ were measured by qRT-PCR.

Figure 17:
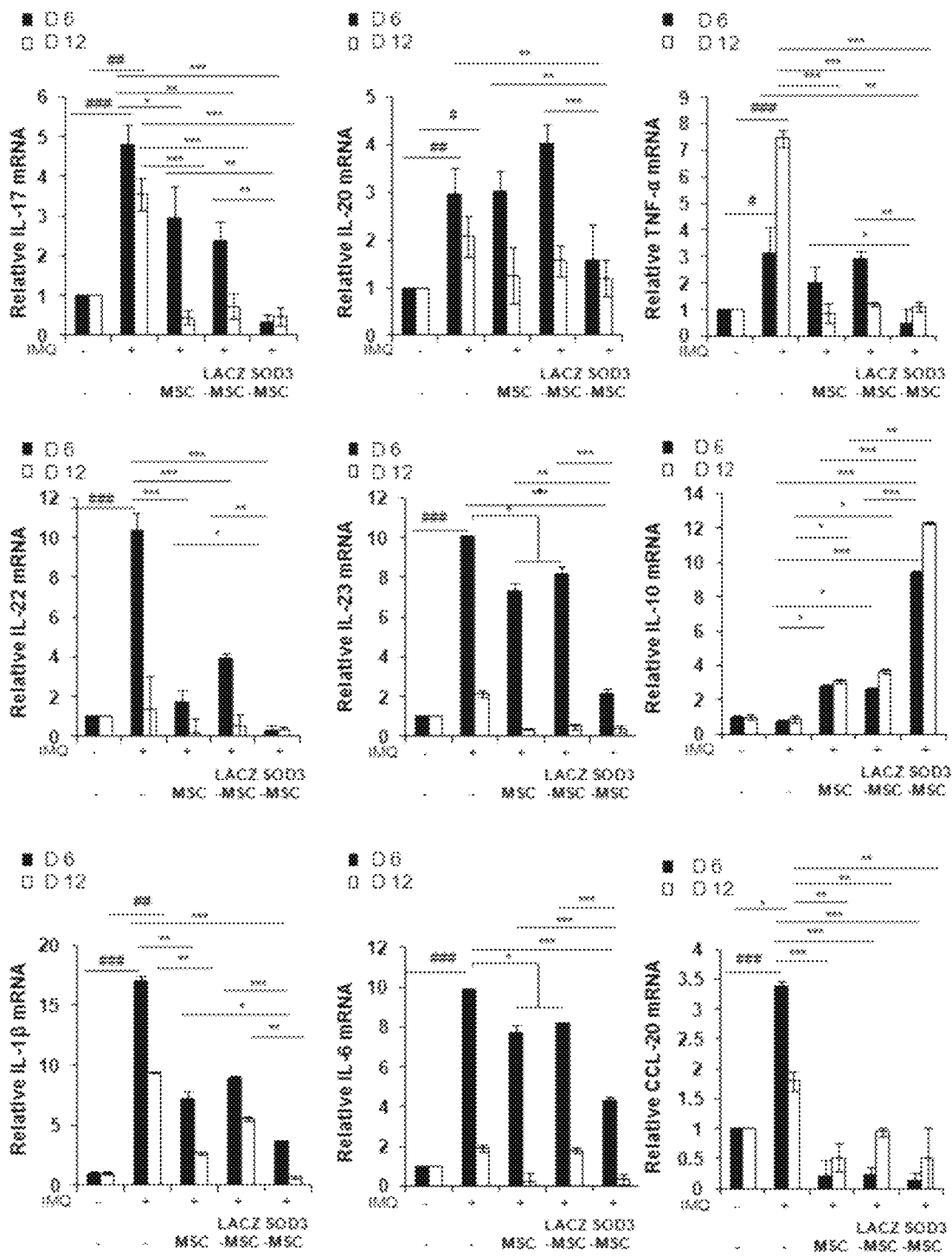
FIG. 17 show graphs depicting RT-PCR results to determine mRNA levels of pro-inflammatory mediators expressed in skin of each group of mice in IMQ-induced chronic and aggressive dermatitis mouse experiments.

As shown in FIG. 17, the RNA levels of various inflammatory cytokines were significantly increased due to IMQ application, and the expression levels of these cytokines had a slight reduction tendency in the mice injected with MSCs or LacZ-MSCs. The inhibitory effect on the expressions of these inflammatory cytokines was observed to be the greatest in the mice injected with SOD3-MSCs compared with the mice injected with the other types of MSCs. Specifically, the expression levels of IL-17 and IL-22, expressed in Th17 cells, and IL-23, IL-1β, IL-6, and TNF-α as major inflammatory mediator cytokines, were observed to be remarkably reduced by SOD3-MSCs.

The expression level of IL-10, which is an anti-inflammatory cytokine and is associated with the inflammation modulation of Treg, was slightly increased due to MSC treatment unlike the other inflammatory cytokines, and the IL-10 increase effect was observed to be excellent in SOD3-MSCs.

The above results indicate that the inflammation-modulating action of MSCs was increased more effectively due to SOD3 introduction, suggesting that the symptoms of inflammation diseases can be alleviated by complexly regulating the expressions and actions of various cytokines.

<2-4> Effect of SOD3-Transfected MSCs on Inflammation-Related Signaling

IMQ has been known to activate TLR-7 and/or TLR-8 and exhibit biological effects through subordinate NFkB signaling systems. Therefore, the effect of the treatment with MSCs, including MSCs overexpressing or not-overexpressing SOD3, on signaling by TLR-7/TRL-8 was investigated by western blot experiments using IMQ-applied skin.

Figure 18:
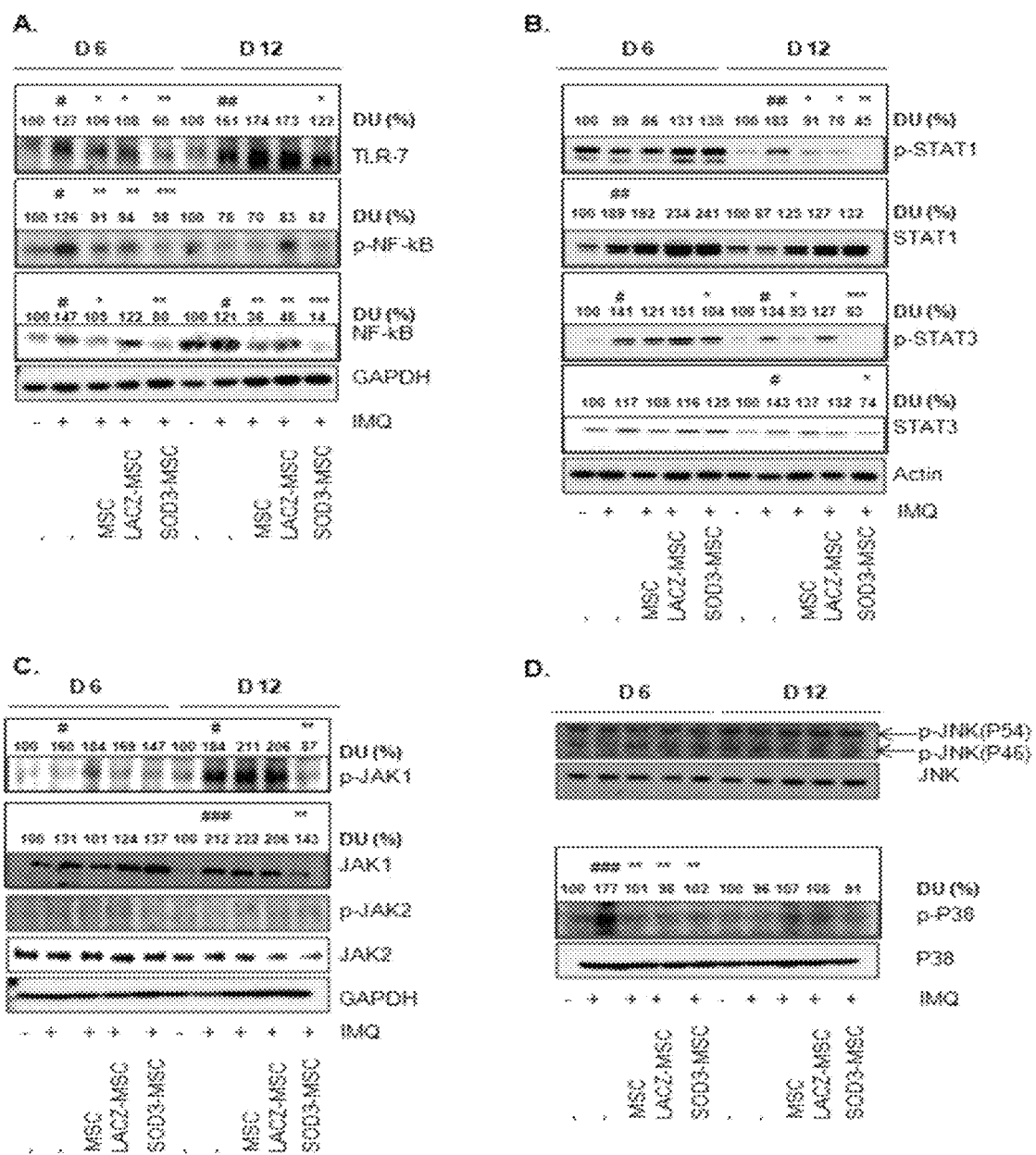
FIG. 18 shows western blot results to depict the expression levels and phosphorylation levels of TLR-7, NF-kB, JNK, p38, STAT1, STAT3, JAK1, and JAK2 present in skin of each group of mice in IMQ-induced chronic and aggressive dermatitis biological model experiments.

As shown in FIG. 18, TLR-7 and phosphorylated NFkB (p-NFkB) were activated and the expression levels thereof were also increased in the back skin of the IMQ-applied mice (FIG. 18A). The signaling of TLR-7 activated by IMQ showed a reduction tendency due to the treatment with MSCs or LacZ-MSCs, and was further reduced by SOD3-MSCs. Similar results were also observed in STAT1/3 and JAK1. However, SOD3-MSCs showed a significant inhibitory effect on, especially, NF-kB signaling systems.

<2-5> cAMP Concentration Increase in Blood Plasma and Cells

Inflammation is triggered when T-helper cells stimulated by antigens infiltrating into the body proliferate to secrete inflammation-inducing substances. The proliferation of T-helper cells occurs by a changed ratio of cAMP to cGMP, which are two substances responsible for cell division. The high cGMP concentration results in faster cell division, and the high cAMP concentration results in slow cell division. The imbalance of such a ratio increases the likelihood of suffering from inflammatory diseases. For example, the cGMP concentration in cells or blood plasma is high in many psoriasis patients. Therefore, the cAMP concentration in the blood plasma of the mice treated with the respective types of MSCs according to the experimental conditions was measured by ELISA.

Figure 19:
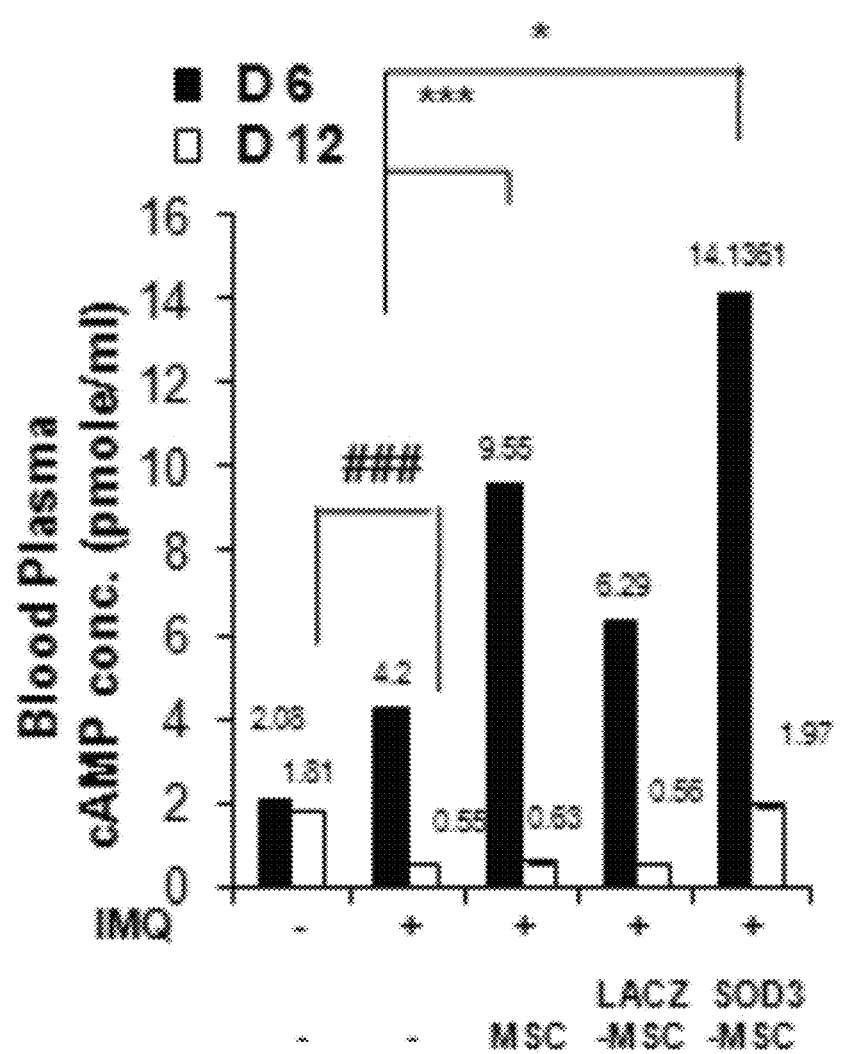
FIG. 19 shows a bar graph depicting cAMP concentration measured in blood plasma of each group of mice in IMQ-induced chronic and aggressive dermatitis biological model experiments.

As shown in FIG. 19, the cAMP level in the blood plasma of the mice injected with MSCs or LacZ-MSCs was increased compared with a control group, and especially, the cAMP level in the blood plasma of the mice injected with SODS-MSCs was observed to be the highest. Such a tendency was more apparent on day 6 of IMQ application. These results mean that SOD3-MSCs have a protective function from cellular stress.

Example 3

Atopic-Like Dermatitis Biological Model Induced by Ovalbumin

The in vivo inflammation regulatory effect of MSCs overexpressing SODS was investigated using other animal models. Atopic-like dermatitis was induced in Balb/C mice using ovalbumin (OVA) as an antigen, and the inflammation inhibitory effects by MSCs were compared and observed.

Figure 20:
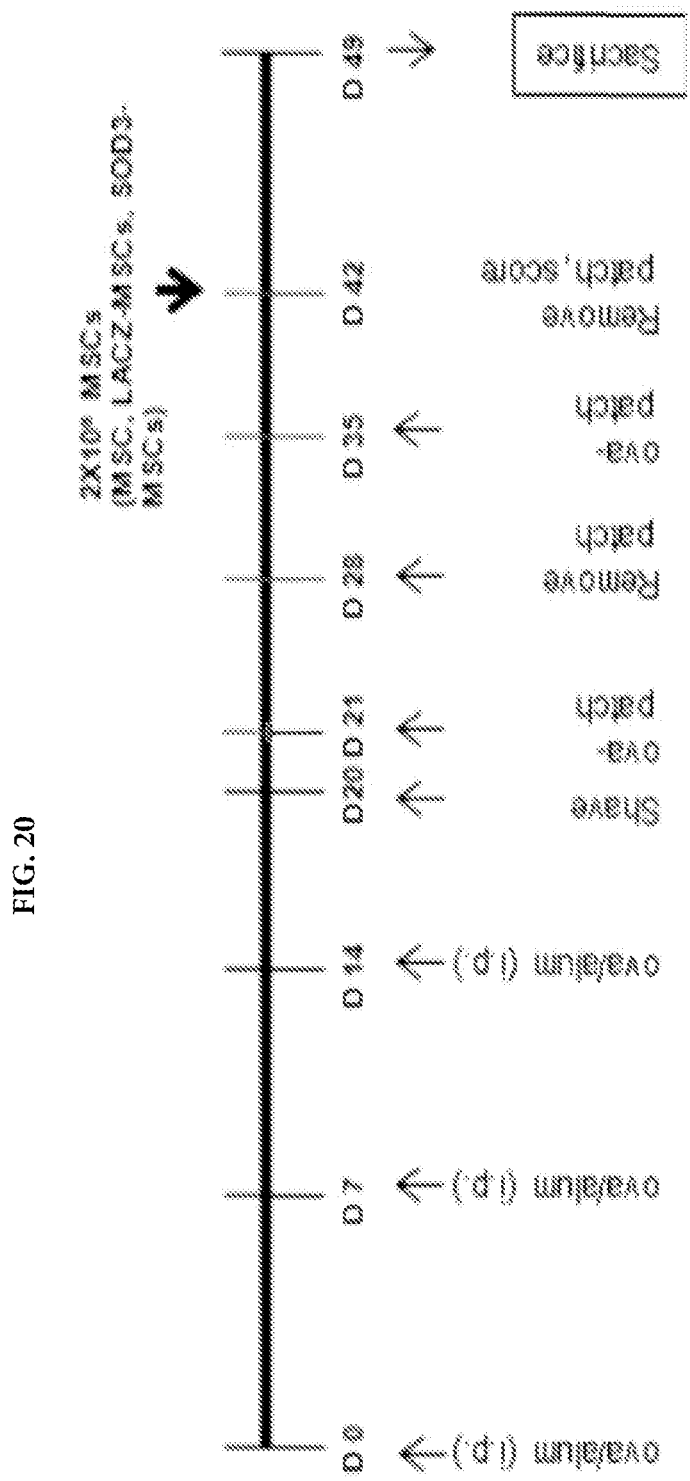
FIG. 20 is a schematic diagram showing an experimental setup for ovalbumin (OVA)-induced atopy-like dermatitis mouse experiments.

According to the experimental setup shown in FIG. 20, a mixture of OVA protein and aluminum hydroxide as an antigen adjuvant was intraperitoneally injected into mice grown in SPF conditions at the start of the experiment (D0), day 7 (D7), and day 14 (D14), so that the animals were sensitized. From day 21 after the start of the experiment, a patch was prepared by wetting 1×1 $cm^2$ gauze in 100 μg of OVA dissolved in 100 μl of PBS, and then attached to the shaved back of the mice to induce immune responses for 7 days. The immune responses were again induced by OVA patch in the same manner for one week starting from day 35. MSCs, LacZ-MSCs, and SOD3-MSCs were injected into the lesion site on day 42 after the start of the experiment (five mice per group) according to the experimental conditions, and skin changes were observed to the naked eye on day 49.

Figure 21:
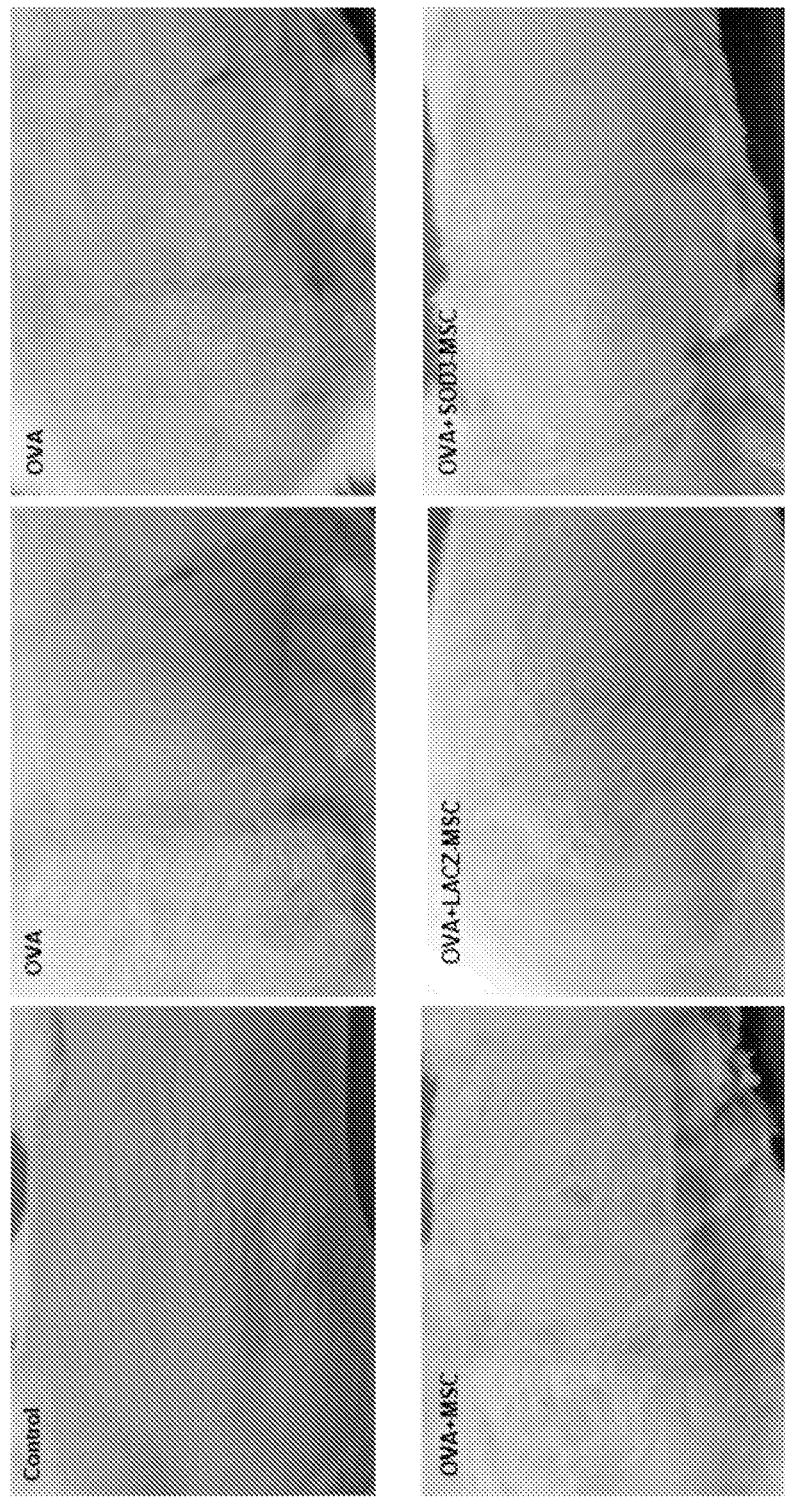
FIG. 21 shows skin images depicting the lesion progression of each group of mice in ovalbumin (OVA)-induced atopy-like dermatitis mouse experiments.

As shown in FIG. 21, skin inflammation including rough skin, scaling, and reddish swelling was progressed on the back skin of the mice treated with only OVA (OVA) without MSC injection compared with a control. The skin inflammation was somewhat alleviated in the mice injected with untreated MSCs (OVA+MSC) or the mice injected with LacZ-MSCs (OVA+LACZ-MSC) compared with the mice treated with only OVA. The skin condition in the mice injected with SOD3-MSCs (OVA+SOD3-MSC) was improved to be similar to that in the control, as scaling and inflammation responses almost disappeared, and especially, an apparent inflammation alleviating effect was confirmed in the mice injected with SOD3-MSCs (OVA SOD3-MSC) compared with the mice injected with the other types of MSCs. The above results indicate that MSCs overexpressing SOD3 have an excellent effect in the alleviation of skin inflammation compared with general MSCs.

INDUSTRIAL APPLICABILITY

The mesenchymal stem cells overexpressing SOD3 have more potent antioxidative activity, immunoregulatory functions, and cellular immunoregulatory functions than general mesenchymal stem cells. The mesenchymal stem cells overexpressing SOD3 can be favorably used in the development of more effective stem cell therapeutics for inflammatory diseases, autoimmune diseases, or transplant rejections.

The invention claimed is:

1. A method for treating an inflammatory skin disease in a subject, the method comprising administering an effective amount of a composition comprising, as an active ingredient, mesenchymal stem cells overexpressing extracellular superoxide dismutase (SOD3) to the subject in need thereof, wherein the inflammatory skin disease is one or more disease selected from the group consisting of psoriasis and atopic dermatitis.

2. The method of claim 1, wherein the mesenchymal stem cells are derived from a tissue selected from the group consisting of umbilical cord, umbilical cord blood, placenta, bone marrow, adipose tissue, muscle, amniotic fluid, and amniotic membrane.

3. The method of claim 1, wherein the SOD3 comprises the amino acid sequence of SEQ ID NO: 1 or SEQ ID NO: 3.

4. The method of claim 1, wherein the mesenchymal stem cells overexpressing SOD3 are obtained by transfecting mesenchymal stem cells with a recombinant expression vector comprising a polynucleotide encoding SOD3.

5. The method of claim 4, wherein the recombinant expression vector is selected from the group consisting of a retrovirus vector, an adenovirus vector, an adeno-associated virus (AAV) vector, a vaccinia virus vector, a herpes virus vector, a lentivirus vector, and an avipox virus vector.

6. The method of claim 4, wherein the polynucleotide encoding SOD3 comprises the nucleotide sequence of SEQ ID NO: 2 or SEQ ID NO: 4.

* * * * *